United States Patent
Blackmore et al.

(10) Patent No.: US 7,565,201 B2
(45) Date of Patent: Jul. 21, 2009

(54) ACTIVATION OF CALCIUM-MEDIATED CELL FUNCTIONS IN CELLS AND TISSUES, INCLUDING AGGREGATION OF HUMAN PLATELETS. BY NANOSECOND PULSED ELECTRIC FIELDS

(75) Inventors: Peter F. Blackmore, Norfolk, VA (US); Stephen J. Beebe, Norfolk, VA (US); E. Stephen Buescher, Virginia Beach, VA (US); Karl H. Schoenbach, Norfolk, VA (US)

(73) Assignees: Eastern Virginia Medical School, Norfolk, VA (US); Old Dominion University, Norfolk, VA (US)

( * ) Notice: Subject to any disclaimer, the term of this patent is extended or adjusted under 35 U.S.C. 154(b) by 662 days.

(21) Appl. No.: 11/305,121

(22) Filed: Dec. 19, 2005

(65) Prior Publication Data

US 2006/0161221 A1 Jul. 20, 2006

Related U.S. Application Data

(60) Provisional application No. 60/636,695, filed on Dec. 17, 2004.

(51) Int. Cl.
*A61N 1/40* (2006.01)
(52) U.S. Cl. ............................. 607/50; 607/72

(58) Field of Classification Search .................. None
See application file for complete search history.

(56) References Cited

U.S. PATENT DOCUMENTS 6,326,177 B1 12/2001 Schoenbach et al.

OTHER PUBLICATIONS

Alermany et al. "Stimulation fo Sphingosine-1-phosphate Formation by the $PSY_2$ Receptor in HL-60 Cells: $Ca^{2+}$Requirements and Implication in Receptor-Mediated $Ca^{2+}$Mobilization, but Not MAP Kinase Activation" Molecular Pharmacology, vol. 58, No. 3, p. 491-497 (2000).
Beebe et al. "Nanosecond Pulsed Electric Field (nsPEF) Effects on Cells and Tissues: Apoptosis Induction and Tumor Growth Inhibition" IEEE Transactions on Plasma Science, vol. 20, No. 1, p. 286-292 (2002).
Beebe et al. "Nanosecond, high-intensity pulsed electric fields induce apoptosis in human cells[1] " The FASEB Journal, vol. 17, p. 1493-1495 (2003).

(Continued)

*Primary Examiner*—Carl H. Layno
*Assistant Examiner*—Jon-Eric C. Morales
(74) *Attorney, Agent, or Firm*—Wilmer Cutler Pickering Hale and Dorr LLP

(57) ABSTRACT

Methods for inducing calcium mobilization in cells through the application of nanosecond pulsed electric fields ("nsPEFs") are provided. The invention also provides a method of increasing intracellular calcium in cells through the application of nsPEFs. In one embodiment of the invention, the cells are human platelets, whereby activation and aggregation of the platelets is induced. Methods for treating an injury, trauma, or loss of blood in a subject, through the application of nsPEFs are also provided.

25 Claims, 22 Drawing Sheets

OTHER PUBLICATIONS

Berridge et al. "Calcium - a life and death signal" Nature, vol. 395 p. 645-648 (1998).

Berridge et al. "Calcium Signalling: Dynamics, Homeostasis and Remodelling" Nature Reviews, Molecular Cell Biology, vol. 4, p. 517-529 (2003).

Bhanot et al., "Current Applications of Platelet Gels in Facial Plastic Surgery" Facial Plastic Surgery, vol. 18, No. 1, p. 27-33 (2002).

Bobanovic et al. "Elementary $[Ca^{2+}]i$ signals generated by electroporation functionally mimic those evoked by hormonal stimulation" The FASEB Journal, vol. 13, p. 365-376 (1999).

Brissett et al. "The effects of tissue sealants, platelet gels, and growth factors and wound healing" Current Opinion in Otolaryngology & Head and Neck Surgey, vol. 11, p. 245-250 (2003).

Buescher et al., poster abstract Bioelectromagnetics Society meeting Jun. 2004.

Deng et al. "The Effects of Intense Submicrosecond Electrical Pulses on Cells" Biophysical Journal, vol. 84, p. 2709-2714 (2003).

Dobrydneva et al. "2-Aminoethoxydiphenyl Borate Directly Inhibits Store-Operated Calcium Entry Channels in Human Platelets" Molecular Pharmacology, vol. 3, p. 541-552 (2001).

Gowrishankar et al. "An approach to electrical medeling of single and multiple cells" PNAS, vol. 100, No. 6, p. 3203-3208 (2003).

Grinstein et al. "Receptor-mediated Activation of Electropermeabilized Neutrophils" The Journal of Biological Chemistry, vol. 263, No. 4, p. 1779-1783 (1988).

Harper et al. "Dihydropyridines as inhibitors of capacitative calcium entry in leukemic HL-60 cells" Biochemical Pharmacology, vol. 65, p. 329-338 (2003).

Heiner et al. "Expression profile of the transient receptor potential (TRP) family in neutrophil granulocytes: evidence for currents through long TRP channel 2 induced by ADP-ribose and NAD" Biochem. J., vol. 371, p. 1045-1053 (2003).

Heiner et al. "Role and regulation of TRP channels in neutrophil granulocytes" Cell Calcium, vol. 33, p. 533-540 (2003).

Itagaki et al. "Sphingosine 1-Phosphate, a Diffusible Calcium Influx Factor Mediating Store-operated calcium Entry" The Journal of Biological Chemistry, vol. 278, No. 30, p. 27540-27547 (2003).

Klinker et al. "G-Protein-coupled Receptors in HL-60 Human Leukemia Cells" Gen. Pharmac., vol. 27, No. 1, p. 33-54 (1996).

Man et al. "The use of Autologous Platelet-Rich Plasma (Platelet Gel) and Autologous Platelet-Poor Plasma (Fibrin Glue) in Cosmetic Surgery" Discussion, vol. 107, No. 1 238-239 (2000).

Man et al. "The Use of Autologous Platelet-Rich Plasma (Platelet Gel) and Autologous Platelet-Poor Plasma (Fibrin Glue) in Cosmetic Surgery" Plastic and Reconstructive Surgery, p. 229-237 (2001).

Mankowski et al. A Review of Short Pulse Generator Technology, IEEE Transactions on Plasma Science, Vol. 28, No. 1, p. 102-108 (2000).

Nilius From TRPs to SOCs, CCEs, and CRACs: Consensus and Controversies, Cell Calcium 33, p. 293-298 (2003).

Schoenbach et al. "Bioelectrics-New Applications for Pulsed Power Technology" IEEE Transactions on Plasma Science, vol. 30, No. 1, p. 293-300 (2002).

Schoenbach et al. "Intracellular Effect of Ultrashort Electrical Pulses" Bioelectromagnetics, vol. 22, p. 440-448 (2001).

Suh et al. "Differential regulation of $P2Y_{11}$ receptor-mediated signalling to phospholipase C and adenylyl cyclase by protein kinase C in HL-60 promyelocytes" British Journal of Pharmacology, vol. 131, p. 489-497 (2000).

Treiman et al. "A tool coming of age: thapsigargin as an inhibitor of sarcoendoplasmic reticulum $CA^{2+}$-ATPases" TiPS, vol. 19, p. 131-135 (1998).

Tsong "Electroporation of Cell Membranes" Biophysical Journal, vol. 60, p. 297-306 (1991).

Venkatachalam et al. "The cellular and molecular basis of store-operated calcium entry" Nature Cell Biology, vol. 4, p. E263-E272 (2002).

Verghese et al. "$P_{2U}$Agonists Induce Chemotasix and Actin Polymerization in Human Neutrophils and Differentiated HL60 Cells" The Journal of Biological Chemistry, vol. 271, No. 26, p. 15597-15601 (1996).

Vernier et al. "Calcium bursts induced by nanosecond electric pulses" Biochemical and Ciophysical Research Communication, vol. 310, p. 286-295 (2003).

ACTIVATION OF CALCIUM-MEDIATED CELL FUNCTIONS IN CELLS AND TISSUES, INCLUDING AGGREGATION OF HUMAN PLATELETS. BY NANOSECOND PULSED ELECTRIC FIELDS

REFERENCE TO RELATED APPLICATIONS

This application claims the benefit of U.S. Provisional Application No. 60/636,695, filed Dec. 17, 2004, the disclosure of which is incorporated herein by reference.

BACKGROUND OF THE INVENTION

Electric fields can be used to manipulate cell function in a variety of ways. One specific cell mechanism that can be affected by electric fields is calcium mobilization within a cell. Calcium signaling, an important cell function, is responsible for a variety of cellular responses and actions. The release of internally stored calcium can stimulate responses to agonists, activate growth and respiration, cause the secretion of neurotransmitters, activate transcription mechanisms, cause the release of a variety of hormones, produce muscle contractions, and initiate release of key factors in the apoptosis pathway (Berridge, M. J., Bootman, M. D., Lipp, P. (1998) Nature. 395, 645-648). This calcium mobilization also triggers the influx of calcium from the external medium into the cell as a means of further propagating calcium signals and also replenishing depleted pools of calcium. Electric fields can be used to manipulate the movement of ions, such as calcium, in order to study calcium signaling.

One application of this calcium increase is to activate platelets and cause them to aggregate in vitro and in vivo. Platelet activation/aggregation is important for preventing blood loss during traumatic injury or surgery by forming a hemostatic plug at the site of injury. At present, treatment with thrombin, known to increase intracellular calcium in human platelets, is used to control slow bleeding at sites of injury. Thrombin treatment includes the topical application of bovine or recombinant thrombin, or the use of platelet gels in which autologous platelets are treated with bovine thrombin and added to the surgical site (Brissett and Hom (2003) *Curr. Opin. Otolaryngol. Head Neck Surgery* 11, 245-250; Man et al., (2001) *Plast. Reconstr. Surg.* 107, 229-237; Saltz (2001) *Plast. Reconstr. Surg.* 107, 238-239; Bhanot and Alex (2002) *Facial Plast. Surg.* 18, 27-33). However, the use of animal products could cause allergic reactions or cause possible contamination of platelet rich plasma (PRP) with infectious agents. The use of recombinant thrombin or a peptide that mimics thrombin action could be used as an alternative to animal-derived thrombin; however, this type of treatment is expensive and could also give rise to allergic reactions.

The use of cauterizing techniques will also seal blood vessels. Surgeons in the operation room commonly use this procedure. The disadvantages of cauterization are that the tissues could be burned and vessels are sealed by coagulation. This procedure induces tissue necrosis, resulting in inflammation, pain, and scarring. There is a need for a non-thermal technique that would not involve cell death, but induce platelet aggregation specifically. Such a technique would not involve sealing blood vessels by cauterization, however it would rely on the patient's own platelets to seal the blood vessel and so prevent blood loss.

Since calcium signaling plays such an important role in so many cellular functions, there remains a need to further examine this signaling mechanism and explore ways to manipulate calcium signaling pathways for therapeutic purposes. For example, there is a need to develop methods of activating calcium-mediated cell functions, including aggregation of human platelets, for therapeutic purposes, such as wound healing. These and various other needs are addressed, at least in part, by one or more embodiments of the present invention.

SUMMARY OF THE INVENTION

One or more aspects of the invention provide a method for inducing calcium mobilization in a cell. The method comprises applying at least one nsPEF to one or more cells, whereby calcium is mobilized in the cells. The at least nsPEF has a pulse duration of at least about 100 picoseconds and no more than about 1 microsecond and an electric field strength of at least about 10 kV/cm and no more than about 350 kV/cm. In one or more embodiments of the invention, calcium influx into the cells occurs.

In one aspect, at least one nsPEF has a pulse duration of about 10 nanoseconds and an electric field strength of about 125 kV/cm. In another aspect, the at least one nsPEF has a pulse duration of about 60 nanoseconds and an electric field strength of about 30 kV/cm.

In one or more embodiments of the invention, at least one nsPEF is applied to the cells. The cells may be suspended in a medium or present as part of a tissue. The cells may be any prokaryotic or any eukaryotic cells, including but not limited to fat cells, bone cells, vascular cells, muscle cells, cartilage cells, stem cells or a combination thereof. The cells may also be abnormal cells, including cancer cells, such as leukemia cells or fibrosarcoma cells.

In one or more aspects of the invention, the cells are human platelets, whereby activation and aggregation of the platelets is induced. In other aspects, the cells are muscle cells, whereby contractions are induced in the muscle cells. In other aspects, the cells are nerve cells, whereby neurotransmitter release is induced in the nerve cells.

The invention also provides a method for increasing intracellular calcium in cells comprising applying at least one nsPEF to the cells, whereby intracellular calcium in the cells is increased. The at least one nsPEF has a pulse duration of at least about 100 picoseconds and no more than about 1 microsecond and an electric field strength of at least about 10 kV/cm and no more than about 350 kV/cm. In one or more embodiments, the cells are human platelets, whereby activation and aggregation of the platelets is induced.

Also provided in the invention is a method for activating and aggregating human platelets comprising applying at least one nsPEF to the platelets, whereby the platelets are activated and induced to form aggregates. The at least one nsPEF has a pulse duration of at least about 100 picoseconds and no more than about 1 microsecond and an electric field strength of at least about 10 kV/cm and no more than about 350 kV/cm. In one aspect, the at least one nsPEF has a pulse duration of about 10 nanoseconds and an electric field strength of about 125 kV/cm. In another aspect, the at least one nsPEF has a pulse duration of about 60 nanoseconds and an electric field strength of about 30 kV/cm. The platelets may be suspended in a medium or included in a tissue.

At least another aspect of the invention provides a method for treating an injury, trauma, or the loss of blood in a subject, comprising applying at least one nsPEF to platelets at the site of injury, trauma, or blood loss, whereby the platelets are activated and induced to form aggregates. The at least one nsPEF has a pulse duration of at least about 100 picoseconds and no more than about 1 microsecond and an electric field strength of at least about 10 kV/cm and no more than about 350 kV/cm.

The invention also provides a method of treating an injury, trauma, or the loss of blood in a subject, comprising applying at least one nsPEF to autologous platelets, whereby the platelets are activated and induced to form aggregates. The activated and aggregated platelets are then applied to the site of injury, trauma, or blood loss. The at least one nsPEF has a pulse duration of at least about 100 picoseconds and no more than about 1 microsecond and an electric field strength of at least about 10 kV/cm and no more than about 350 kV/cm. The blood loss in a subject may be related to a bleeding disorder resulting from inactive platelets or low platelet counts. The blood loss may also be related to a platelet disorder such as congenital afibrinogenemia, Glanzmann's thrombasthenia, gray platelet syndrome, and Hermansky-Pudlak syndrome.

DETAILED DESCRIPTION OF THE INVENTION

Figure 1:
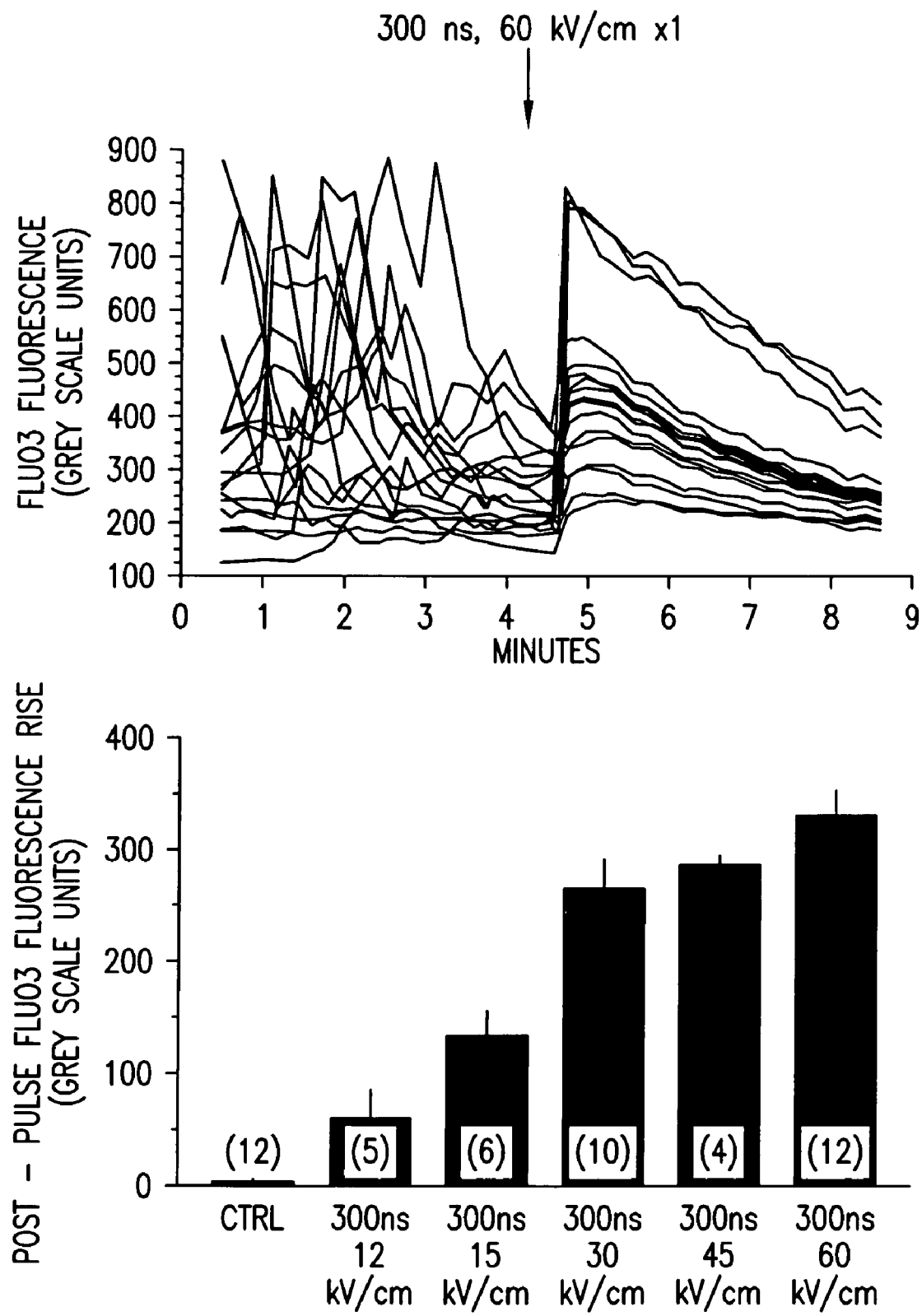
FIG. 1 describes the qualitative $[Ca^{2+}]_i$ responses of polymorphonuclear leukocytes (PMNs) to nsPEF applications. Fluo3 labeled PMNs were examined by fluorescence microscopy before and following a single 300 ns, 60 kV/cm pulse application (upper panel). Application of a single nsPEF to the cells resulted in a rapid, variable increase in $[Ca^{2+}]_i$ that waned in most cells over 4-5 minutes, loss of spontaneous fluctuations in $[Ca^{2+}]_i$ and immediate loss of cellular movement. The lower panel shows dose-response relationship between intensity of the single pulse and the mean±S.E.M. post-pulse rise in Fluo3 fluorescence. Numbers in parentheses overlying the bases of the bars indicate the number of experiments performed.

For the purposes of promoting an understanding of the principles of the invention, reference will now be made to preferred embodiments and specific language will be used to describe the same. It will nevertheless be understood that no limitation of the scope of the invention is thereby intended. Rather, such alterations and further modifications of the invention, and such further applications of the principles of the invention as illustrated herein, as would be contemplated by one having skill in the art to which the invention relates are intended to be part of the present invention.

For example, features illustrated or described as part of one embodiment can be used on other embodiments to yield a still further embodiment. Additionally, certain features may be interchanged with similar devices or features not mentioned yet which perform the same or similar functions. It is therefore intended that such modifications and variations are included within the totality of the present invention.

One or more embodiments of the present invention are directed to a method of inducing calcium mobilization in a cell using nanosecond pulsed electric fields ("nsPEFs"). "Calcium mobilization" as used herein is defined as the release of internally stored calcium in cells and/or the influx of calcium from the external medium into the cell. In one or more embodiments of the invention, calcium mobilization leads to an increase in intracellular free calcium levels of cells.

An "nsPEF" or "nanosecond pulsed electric field" as used herein is defined as an electric pulse in the nanosecond range (about 100 picoseconds to about 1 microsecond) with electric field intensities from about 10 kV/cm to about 350 kV/cm. For delivery of nsPEFs to cells, any apparatus equipped with a pulse generator that can deliver short electrical pulses of pulse duration of at least about 100 picoseconds and no more than about 1 microsecond, and of electric field strength of at least about 10 kV/cm and no more than about 350 kV/cm, may be used. In another aspect of the invention, the pulse generator can deliver short electrical pulses of pulse duration of at least about 100 picoseconds and no more than about 1 microsecond, and of electric field strength of at least about 10 kV/cm and no more than about 30 kV/cm. In another aspect of the invention, the pulse generator can deliver short electrical pulses of pulse duration of at least about 100 picoseconds and no more than about 1 microsecond, and of electric field strength of at least about 10 kV/cm and no more than about 125 kV/cm. In another aspect of the invention, the pulse generator can deliver short electrical pulses of pulse duration of at least about 10 nanoseconds and no more than about 300 nanoseconds, and of electric field strength of at least about 10 kV/cm and no more than about 30 kV/cm. In another aspect of the invention, the pulse generator can deliver short electrical pulses of pulse duration of at least about 10 nanoseconds and no more than about 300 nanoseconds, and of electric field strength of at least about 10 kV/cm and no more than about 125 kV/cm. In another aspect of the invention, the pulse generator can deliver short electrical pulses of pulse duration of about 10 nanoseconds and an electric field strength of about 125 kV/cm. In another aspect of the invention, the pulse generator can deliver short electrical pulses of pulse duration of about 60 nanoseconds and an electric field strength of about 30 kV/cm.

The apparatus for delivery of nsPEFs is also equipped with a high voltage power supply and with a means for directing the nsPEFs to the target cells in vitro or in vivo. Preferably, the target cells are in situ, and any suitable means for directing the nsPEFs to the in vitro, in vivo and/or in situ target cells may be employed. Suitable means for directing the nsPEFs will preferably allow high voltage, short duration electrical pulses in the nanosecond range, for example, in cell suspensions or within tissues. Examples include an electrode system, such as needles or needle arrays. In one or more embodiments of the invention, the nsPEFs are applied to cells suspended in a medium. In other embodiments, the nsPEFs are applied directly to cells present as part of a tissue. In other embodiments, the nsPEFs are applied to autologous platelets, thereby activating the platelets and inducing them to form aggregates, and the activated and aggregated platelets are then applied to a site of injury, trauma, or blood loss. In other embodiments, the nsPEFs are applied directly to the site where bleeding is occurring.

The nsPEF pulses of the present invention can be administered to the cells by means of a pulse generator, such as the generator previously described in U.S. Pat. No. 6,326,177 and Beebe et al. *FASEB J.* 17, 1493-1495 (2003). Prior to the above-described pulse generator, the application of these high frequency intracellular effects had been limited due to the difficulty of generating large intracellular electric fields on a time scale that is comparable to or even less than the charging time of the surface. However, as described in U.S. Pat. No. 6,326,177 and Beebe et al. (2003), the present inventors developed technology for generating high voltage, short duration electrical pulses that make it possible to produce electric pulses in the nanosecond range with voltage amplitudes adequate to generate electric fields near MV/cm in suspensions of cells or within tissues (Mankowski, J., Kristiansen, M. (2000) *IEEE Trans Plasma Science* 28:102-108). Because of their nanosecond duration, the average energy transferred to the cells/tissues by these pulses is theoretically negligible, resulting in electrical effects without accompanying thermal effects.

The electric field strength (or electric field intensity) of the nsPEF pulse to be applied to cells is the applied voltage divided by the distance between the electrodes, and is generally at least about 10 kV/cm, but should not exceed the breakdown field of the suspension or tissue which includes the cells. The breakdown field increases with decreasing pulse duration, and can be experimentally determined. Under the conditions commonly employed in the present invention, however, the breakdown field generally does not exceed 500 kV/cm. In one or more aspects of the invention, electric field pulses which have durations of about 100 picoseconds to about 1 microsecond typically have electric field strengths of about 10 kV/cm to about 350 kV/cm.

To minimize the potential effects on the bulk temperature of the medium ("thermal effects"), the electric field pulses generally have a rapid rise time and short duration. The pulses should preferably be less than one microsecond, but more than about 100 picoseconds in duration. In one or more aspects of the invention, a pulse duration is about 1 nanosecond to about 300 nanoseconds. The optimum pulse duration will vary depending on the cell type, tissue type, and desired treatment, among other factors.

The number of nsPEF pulses to be applied to the cells is that sufficient to induce calcium mobilization. This number may vary based on a variety of factors included the intended effect, the mode of administration of the nsPEFs, and the cells to be treated. In one aspect of the invention, at least one nsPEF is applied to the cells to induce calcium mobilization. In another aspect of the invention, at least two nsPEFs are applied to the cells. In another aspect of the invention, at least five nsPEFs are applied to the cells. In another aspect of the invention, at least ten nsPEFs are applied to the cells. In yet another aspect of the invention, 1-10 nsPEFs are applied to the cells.

Notably, the nsPEFs are distinct from electroporation pulses based on their temporal and electrical characteristics, as well as their effects on intact cells and tissues. For comparative purposes, electroporation pulses and nsPEFs, respectively, exhibit different electric field strength (1-5 kV/cm vs. 10-350 kV/cm); different pulse durations (0.1-20 milliseconds vs. 1-300 nanoseconds); different energy densities (joules/cc vs. millijoules/cc) and different power (500 W vs. 180 MW). Thus, nsPEFs can be five to six orders of magnitude shorter with electric fields and power several orders of magnitude higher and energy densities considerably lower than electroporation pulses. In addition to the unique short duration and rapid rise time, nsPEFs are exceptional because they are very low energy and extremely high power. Stemming from these differences, as the pulse duration decreases, nsPEFs bypass the plasma membrane and target intracellular structures such as the mitochondria, endoplasmic reticulum, Golgi apparatus, nucleus, or any intracellular store, leaving the plasma membrane intact. These pulses have effects that are unexpectedly different than those of electroporation pulses because, when the pulse duration is short enough and the electric field intensity is high enough, intracellular structures are targeted. The effects of nsPEFs on cells differ depending on the cell type, pulse duration and risetime, electric field intensity, and/or other factors.

In addition, nsPEFs and electroporation pulses have different effects on cells. For example, Jurkat cells exposed to classical electroporation pulses (e.g. 100 μs) exhibited immediate propidium iodide ("PI") uptake, but when exposed to 60 or 300 ns they took up PI at much later times, consistent with apoptosis induction (Deng, J., et al. (2003), *Biophys. J.* 84, 2709-2714). Furthermore, in contrast to classical electroporation effects where larger cells are more readily electroporated than smaller cells, nsPEFs have greater plasma membrane effects on smaller cells (e.g. T-cells) than larger ones (e.g. monocytes). Under conditions that are independent of plasma membrane electroporation, nsPEFs have been shown to alter signal transduction mechanisms that determine cell fate. Using nsPEFs, it is possible to trigger apoptosis (Beebe, S. J., et al. (2002), *IEEE Trans. Plasma Sci.* 30:1 Part 2, 286-292; Beebe, S. J., et al. (2003), *FASEB J* (online, Jun. 17, 2003) 10.1096//fj.02-0859fje; Vernier, P. T., et al. (2003), *Biochem. Biophys. Res. Comm.* 310, 286-295). nsPEFs induced several well-characterized apoptosis markers including intact plasma membranes, annexin-V-FITC binding, caspase activation, cell shrinkage, cytochrome c release into the cytoplasm, and ultimately, a late secondary necrosis as defined by rupture of the plasma membrane in vitro in the absence of phagocytosis (Beebe et al., 2003).

The methods of inducing calcium mobilization described herein may be used for a variety of cell types. In one embodiment, mammalian cells are used. For example, the methods described herein can be used to effect calcium mobilization in all prokaryotic and eukaryotic cells, including but not limited to, fat cells, bone cells, vascular cells, muscle cells, cartilage cells, and stem cells. The methods can also be used to effect calcium mobilization in abnormal cells, including cancer cells, such as leukemia cells and fibrosarcoma cells.

One or more embodiments of the invention are directed to a method of activating and aggregating platelets through the use of nsPEFs. In human platelets, nsPEF-induced calcium mobilization was found to induce platelet activation and aggregation, thereby providing a mechanism to clot blood and heal wounds. Accordingly, in one embodiment, the invention is directed to a method of activating and aggregating platelets comprising the application of nsPEF pulses to the cells to induce platelet activation and/or platelet aggregation. In another embodiment, the invention may be used in any clinical situation where there is any site of injury, trauma, or blood loss, either induced during surgery or as the result of trauma that results in the loss of blood. In some embodiments, the invention involves either the direct application of electrodes at the site of injury, trauma, or blood loss and/or electrically pulsing autologous platelets and applying these at the site of injury, trauma, or blood loss.

Other embodiments of the invention involve the use of nsPEFs in patients with bleeding disorders that are the result of either inactive platelets or low platelet counts (thrombocytopenia). Other platelet disorders, although rare, that may be treated with nsPEFs include congenital afibrinogenemia, Glanzmann's thrombasthenia, gray platelet syndrome, and Hermansky-Pudlak syndrome.

In another embodiment of the invention, nsPEF-induced calcium mobilization is used to modulate neurotransmitter release from the nerve terminal since the increase in internal calcium levels stimulates neurotransmitter release. In this embodiment, the nsPEFs are contacted to the cells to be treated, which induces calcium mobilization and calcium influx into the cell in an amount sufficient to stimulate neurotransmitter release.

In another embodiment, nsPEF pulses can be used to elevate internal calcium levels in muscle cells, thereby causing muscle contractions. In this embodiment, muscle cells are contacted with nsPEFs, which induces calcium mobilization and calcium influx into the cell in an amount sufficient to induce muscle contractions.

Applications of the present invention further include, but are not limited to, stimulating neurotransmitter release, stimulating hormone release, stimulating cell respiration and proliferation, producing muscle contractions, transcribing genes and use in vaccine administration for efficient delivery and/or enhanced secretion of antigen. As explained above, calcium signaling is involved in a variety of cellular activities; therefore, nsPEF induced internal calcium mobilization can be used to modulate a wide variety of calcium-dependent cell activities.

Reference will now be made to specific examples illustrating the use of nsPEFs in inducing calcium mobilization in a cell. It is to be understood that the examples are provided to illustrate preferred embodiments and that no limitation of the scope of the invention is intended thereby.

EXAMPLE 1 nsPEFs Induce Increases in Intracellular Calcium Using Human Neutrophils

FIG. 1 demonstrates qualitative $[Ca^{2+}]_i$ responses of polymorphonuclear leukocytes (PMNs) to nsPEF applications. Fluo3 labeled PMNs were examined by fluorescence microscopy before and following a single 300 ns, 60 kV/cm pulse application (upper panel). Each line is the grey-scale intensity (averaged over a spot (17 pixel diameter) within the cell) representation of intracellular Fluo3 fluorescence observed in one cell in the microscopic field. The highly variable Fluo3 fluorescence observed from cell-to-cell is due to changes in $[Ca^{2+}]_i$ as the cells moved on the pulsing electrode surface. Application of a single nsPEF to the cells resulted in a rapid, variable increase in $[Ca^{2+}]_i$ that waned in most cells over 4-5 minutes, loss of spontaneous fluctuations in $[Ca^{2+}]_i$ and immediate loss of cellular movement. Lower panel shows dose-response relationship between intensity of the single pulse and the mean±S.E.M. post-pulse rise in Fluo3 fluorescence.

A single nsPEF application (300 ns, 60 kV/cm) induced an immediate, transient rise in the intracellular free $Ca^{2+}$ concentration ($[Ca^{2+}]_i$). In experiments where the cells were actively crawling over the slide cuvette surface (with associated fluctuations in $[Ca^{2+}]_i$ prior to pulse application, this activity abruptly ceased coincident with the pulse-induced rise in $[Ca^{2+}]_i$ and the cells remained non-motile for the subsequent 7-10 minutes of the experiment. In dose/response experiments, decreasing the pulse intensity (300 ns, 15 kV/cm) resulted in smaller transient rises in $[Ca^{2+}]_i$ with reappearance of spontaneous movement and changes in $[Ca^{2+}]_i$ reappearing in some cells prior to completion of the experiment. These results suggest that nsPEF applications can affect $[Ca^{2+}]_i$ and cellular function, and that the effects on cell function are reversible depending on the pulse parameters used. The results also indicate that nsPEF-induced calcium elevation in neutrophils that interrupts or confuses orchestrated cell signaling mechanisms, which modulate cell movement or chemotaxis. This could be used to block neutrophil function in a reversible or irreversible way, depending on the pulse conditions.

EXAMPLE 2

Investigation of nsPEF-induced Apoptosis and Caspase Activation in Order to Determine whether Calcium-dependent or Calcium-independent Cellular Mechanisms were being Activated During Apoptosis Materials and Methods Cell culture—Non-transformed HL-60 and Jurkat cells were obtained from and cultured as recommended by American Type Culture Collection (ATCC, Rockville, Md.) as previously described (Beebe, S. J., et al. (2002). *IEEE Trans. Plasma Sci.* 30:1 *Part* 2, 286-292; Beebe, S. J., et al. (2003). *FASEB J.* 17, 1493-1495). Cells were removed from log phase growth and suspended in Hanks Balanced Salt Solution (HBSS) in the presence or absence of $Ca^{2+}$ and $Mg^{2+}$. When calcium was omitted, cells were washed several times in buffer without added calcium. In other experiments, the calcium chelator BAPTA was added to chelate intracellular calcium. Cells were loaded with BAPTA-AM and washed in HBSS before the addition of agonists.

Administration of nsPEF—Cell suspensions ($7.7 \times 10^6$ cells/ml; $10^6$ cells/130 µl) were loaded into the BioRad Gene Pulser® cuvettes (Bio-Rad Laboratories, Hercules, Calif.) prior to nsPEF pulsing. nsPEF was delivered to the load, a 0.1, 0.2, or 0.4 cm cuvette containing cell suspension, by means of a cable pulse generator as previously described (Beebe et al., 2003). Briefly, the generator consists of a pulse-forming network (PFN),—five 50Ω cables in parallel and a spark gap in atmospheric air as a nanosecond closing switch. Post pulse the cell suspension was removed from the pulsing cuvette and assayed.

Determination of caspase activation in vivo—Caspase activity was determined in vivo using a fluorescent-labeled, irreversible caspase inhibitor, VAD-fmk-FITC (Val-Ala-Asp-fluoromethylketone labeled with fluoroisothiocyanate) that is specific for the active site of the enzyme (see Beebe et al., 2003). Briefly, cells were exposed to nsPEF, incubated in the presence of the fluorescent caspase inhibitor for 20 minutes, washed to remove background fluorescence and subjected to flow cytometry. Values are expressed as the geometric mean FITC fluorescence.

Determination of caspase activation in vitro—Caspase activity was determined in vitro from fibrosarcoma tumor extracts after exposure to nsPEF. Extracts were prepared from tissue homogenates and assayed for caspase activity using the fluorescent substrate DEVD-afc as previously described (Parvathanani et al. 1998). Briefly, extracts were incubated with 50 µM DEVD-AFC (Asp-Glu-Val-Asp-AFC) and fluorescence (excitation 400 nm and emission 505 nm) was determined. Caspase units were defined as pmols of substrate cleaved/min/mg extract protein.

Figure 2:
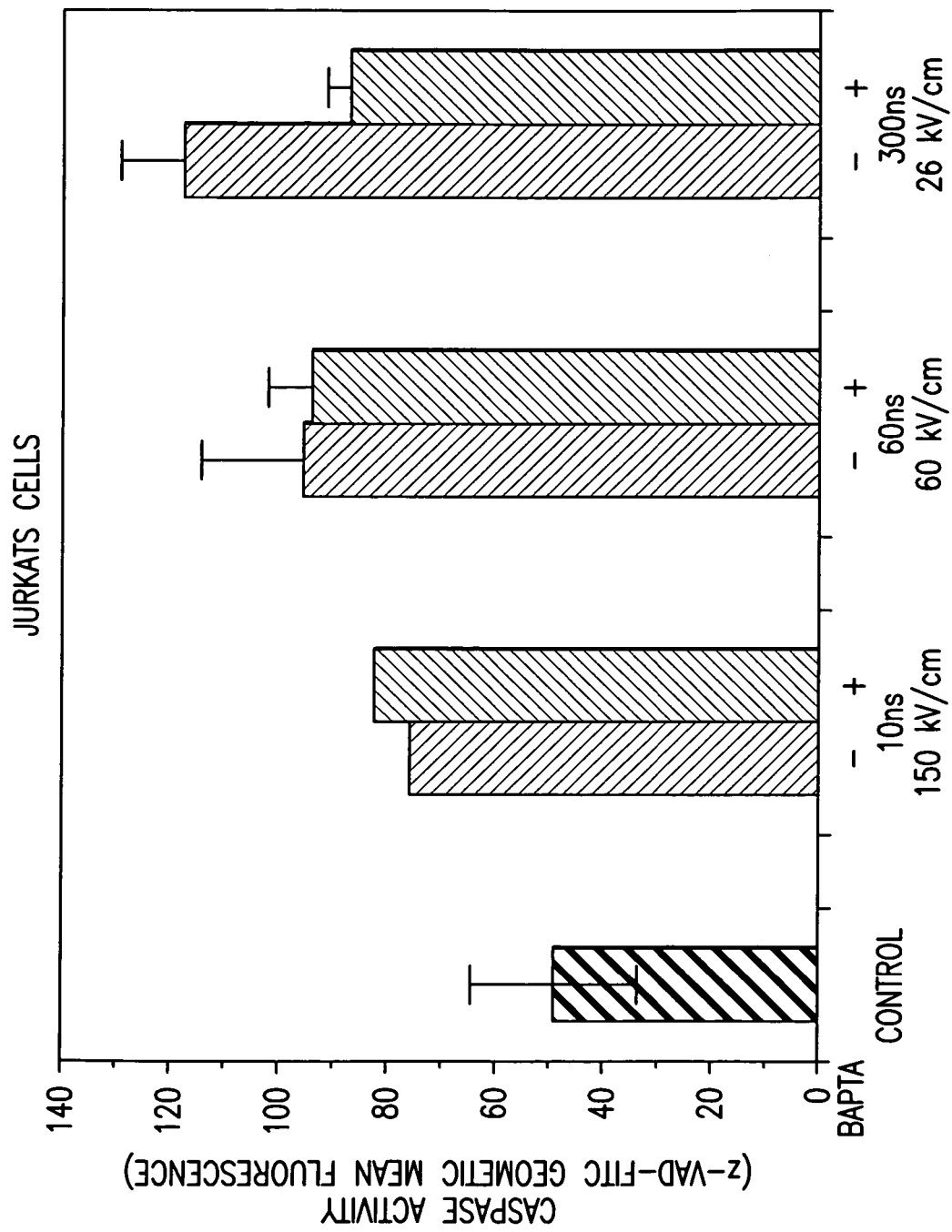
FIG. 2 describes the effect of intracellular calcium chelation by BAPTA on caspase activation in human Jurkat cells. Jurkat cells were incubated with BAPTA-AM (10 mM) in Hanks Balanced salt solution (HBSS) with calcium for 30 minutes and washed in HBSS with calcium. The BAPTA loaded cells were exposed to nsPEF as indicated. The electric fields were adjusted to provide a similar energy density (~1.7 J/cc) under all conditions. After exposure to nsPEF, the cells were incubated with a cell permeable, irreversible inhibitor of active caspases, z-VAD-FITC for 20 minutes before analysis by flow cytometry (Beebe et al., (2003) *FASEB J* 17, 1493-1495). The values for caspase activity are expressed as the geometric mean z-VAD-FITC fluorescence determined in 15,000 individual cells.

Results of Caspase Activation Experiments nsPEFs-induced apoptosis in cultured cells does not require calcium. It was previously demonstrated using several different apoptosis markers, that nsPEF can induce apoptosis in cultured cells (Beebe et al., 2002, 2003). In Jurkat and HL-60 cells, intact cells expressed externalization of phosphatidylserine, caspase activation, and a decrease in forward light scatter, which was consistent with cell shrinkage, another apoptosis cell marker. In addition, cytochrome c was released from the mitochondria into the cytoplasm. This demonstrated that nsPEF-induced caspase activation was mitochondrial-dependent. To determine if caspase activation was calcium dependent, cells first were exposed to nsPEF with durations of 60 ns and 60 kV/cm in the presence and absence of extracellular calcium. Annexin-V-FITC binding and caspase activation were unaffected by the absence of calcium, suggesting that apoptosis was calcium-independent. However, it was possible that Jurkat cells utilized calcium from intracellular stores during apoptosis. To further test the possible role of calcium in Jurkat and HL-60 cell apoptosis, cells were incubated with the calcium-chelating agent BAPTA-AM. BAPTA-AM enters the cell, the acetoxymethyl (AM) ester groups are cleaved by intracellular esterases trapping BAPTA inside the cell. In these experiments the electric fields were adjusted to equalize the energy density at ~1.7 J/cc for 10, 60, and 300 ns pulse durations. In Jurkat cells (FIG. 2), BAPTA had no significant effect on caspase activation for pulses at 10 and 60 ns. In contrast, BAPTA significantly reduced caspase activity by about 25% for pulses with 300 ns durations. These results are consistent with the hypothesis that at longer pulse durations multiple apoptosis pathways are recruited by nsPEF, most likely including mechanisms at the plasma membrane and intracellular membranes while shorter durations recruit mechanisms that are predominantly intracellular.

Figure 3:
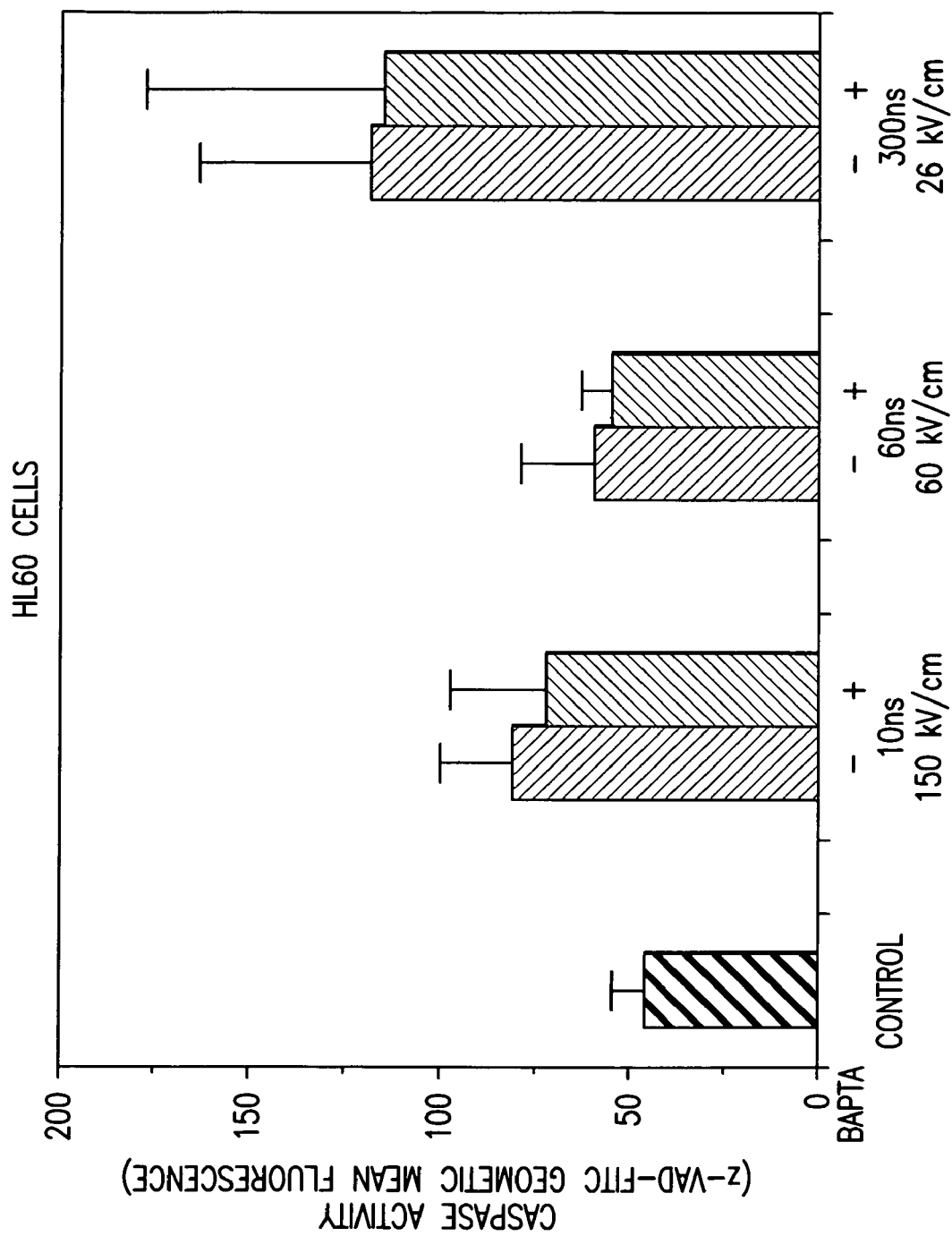
FIG. 3 exhibits the effect of intracellular calcium chelation by BAPTA on caspase activation in human HL-60 cells. Experiments with HL-60 cells in the presence and absence of BAPTA cells were carried out as described for Jurkat cells in FIG. 2 (n=4).

In HL-60 cells (FIG. 3), BAPTA did not significantly affect caspase activity for pulses at 10, 60 and 300 ns when electric fields were adjusted to equalize the energy density, suggesting calcium-independent apoptosis in these cells. To be certain that BAPTA was able to chelate all intracellular calcium, two agents that mobilize calcium by two different mechanisms were used and the calcium concentration in the cell was directly measured using the fluorescent calcium indicator fura-2. Cells were loaded with Fura2 and BAPTA and tested in media without calcium. The first agonist tested was the purinergic agonist ATP, which leads to the release of intracellular calcium through a phospholipase C- and $IP_3$-mediated mechanism through the $IP_3$ receptor in the endoplasmic reticulum (Berridge, M. J. et al. (1998) Nature 395, 645-648). This is followed by an influx of calcium through store-operated calcium channels in the plasma membrane. ATP induced a rapid and transient increase in calcium in the absence of BAPTA. In the presence of BAPTA, the basal calcium level was reduced and the calcium mobilization was completely inhibited. The second agonist tested was cyclopiazonic acid (CPA), which causes increases in calcium by inhibiting the calcium-ATPase in the endoplasmic reticulum. This pump replenishes the intracellular calcium stores after actions by calcium-mobilizing agents. In the absence of BAPTA, CPA caused a slow and sustained release of calcium. In the presence of BAPTA, basal calcium levels were lower and the CPA-mediated calcium mobilization was completely inhibited. Thus, BAPTA inhibited rapid and transient as well as slow and sustained calcium mobilization by agents that acted on a plasma membrane receptor and an endoplasmic reticulum calcium pump. These results suggest that there are cell type-specific differences for calcium-mediated apoptosis mechanisms, but indicate that nsPEF-induced apoptosis can proceed in the absence of calcium.

Discussion

Previous studies indicated that nsPEF-induced apoptosis involves mitochondrial release of cytochrome c, and caspase activation (Beebe et al., 2002, 2003). Roles for calcium in apoptosis induction have been well documented, but calcium-independent apoptosis mechanisms have also been characterized. As shown here, nsPEF-induced apoptosis involves calcium-independent and/or calcium-dependent mechanisms. Chelation of intracellular calcium by BAPTA had no effect on nsPEF-induced caspase activation in HL-60 cells and only slightly, but significantly reduced caspase activation in Jurkat cells. These findings indicate that apoptosis as determined by caspase activation in both cell types does not require calcium, but calcium dependent mechanisms may be operative in some cell types.

EXAMPLE 3

Investigation of nsPEF Stimulation at Electric Fields Below the Threshold for Apoptosis in Order to Explore Non-apoptotic Internal Calcium Responses to nsPEF The effects of nsPEFs on the release of internal calcium and activation of calcium influx in HL-60 cells were also investigated using real-time fluorescent microscopy with Fluo-3 and fluorometry with Fura-2. nsPEFs induced an increase in intracellular calcium levels that was seen in all cells. With pulses of 60 ns duration and electric fields between 4 and 15 kV/cm, intracellular calcium increased 200 nM-700 nM, respectively, above basal levels (~100 nM) while the uptake of propidium iodide was absent. This suggests that increases in intracellular calcium were not due to plasma membrane electroporation. nsPEF and the purinergic agonist UTP induced calcium mobilization in the presence and absence of extracellular calcium with similar kinetics and appeared to target the same $IP_3$- and thapsigargin-sensitive calcium pools in the endoplasmic reticulum. For cells exposed to either nsPEF or UTP in the absence of extracellular calcium, there was an electric field-dependent or UTP-dose dependent increase in capacitative calcium entry when calcium was added to the extracellular media. Although not intending to be bound by a particular theory, these findings suggest that the plasma membrane calcium influx channels are activated by the initial calcium release induced by nsPEFs or ligand-mediated responses, which access similar internal calcium pools, at least in part, by activating capacitative calcium entry (CCE). nsPEFs affect intracellular structures in living cells providing a new means to modulate cell signal transduction mechanisms and regulate cell function.

To compare nsPEF induced-responses on intracellular free calcium ($[Ca^{2+}]_i$) the purinergic agonist UTP (Alemany R., et al. (2000) *Mol. Pharmacol.* 58, 491-497; Verghese M. W., et al. (1996) *J. Biol. Chem.* 271, 15597-15601), which has previously been shown to induce calcium fluxes in HL-60 cells, was used. Purinergic agonists induce calcium signaling by binding to a specific purinergic receptor of the $P2Y_2$ [previously called $P_{2U}$] subtype. $P2Y_2$ receptors were previously shown to be present in HL-60 cells (Suh, B. C., et al. (2000) *Br. J. Pharmacol.* 131, 489-497). Purinergic stimulation of HL-60 cells with UTP has been shown to increase intracellular free calcium ($[Ca^{2+}]_i$) (Klinker, J. F., et al. (1996) *Gen. Pharmac.* 27, 33-54). This receptor signaling involves G-protein activation of phospholipase C (PLC) with a subsequent increase in the second messenger inositol-1,4,5-trisphosphate ($IP_3$) (Berridge, M. J. (2003) *Nat. Rev. Mol. Biol.* 4, 517-529). $IP_3$ then initiates the release of $IP_3$-sensitive calcium stores in cellular organelles, such as the endoplasmic reticulum, releasing their calcium into the cytosol. This increase in calcium stimulates the opening of store-operated channels in the plasma membrane allowing influx of calcium into the cell for replenishment of the internal stores. This influx is believed to be via a capacitative calcium entry (CCE) mechanism. The precise molecular nature of the CCE pathway in many cells is unknown. However, there is much evidence suggesting that members of the transient receptor potential (TRP) family of proteins may act as the plasma membrane calcium channel. The TRP proteins are classified as TRPC (canonical), TRPV (vanilloid) and TRPM (melastatin) (Nilius B. (2003) *Cell Calcium* 33, 293-298). The transmembrane architecture of the TRPs is similar to voltage-gated and cyclic nucleotide gated channels. HL-60 cells are positive for TRPC1, TRPC2, TRPC3, TRPV1, TRPV2, TRPV5, TRPV6, and TRPM2 (Heiner I., et al. (2003) *Biochem J.* 371, 1045-1053). From this collection of channel proteins, TRPC1, TRPC3, TRPC4 and TRPV6 have been shown to participate in CCE (Heiner I., et al. (2003) *Cell Calcium* 33, 533-540). Therefore, HL-60 cells possess several candidates that could act as CCE channels.

How the internal calcium store depletion communicates to the CCE process in the plasma membrane is still being studied. Two main theories exist for this coupling including a physical interaction between the $IP_3$ receptor in the endoplasmic reticulum and the CCE channel and the second suggests the existence of a secondary messenger molecule or calcium inducing factor (CIF) (Itagaki, K., Hauser, C. J. (2003) *J. Biol. Chem.* 278, 27540-27547; Venkatachalam, K., et al. (2002) *Nat. Cell Biol.* 4, E263-72).

Preliminary studies showed nsPEF stimulation of HL-60 cells increased $[Ca^{3+}]_i$. The purpose of this study was to investigate the mechanism by which nsPEF increased $[Ca^{2+}]_i$. The data show that nsPEF can induce calcium transients similar to those seen using traditional chemical agonists such as purinergic receptor agonists and thapsigargin. This response was observed in the absence of classical plasma membrane electroporation. Previous studies in HeLa cells showed that classical electroporation pulses (100 μs, 500 V/cm) also stimulated calcium responses similar to those seen with hormones (Bobanovic, F., Bootman, M. D., Berridge, M. J., Parkinson, N. A., Lipp, P. (1999) *FASEB J.* 13, 365-76). The results presented here further support the hypothesis that when nanosecond pulsed electric fields are intense enough, intracellular signal transduction cascades can be triggered, resulting in signaling events that are common with natural ligands. The application of nsPEFs to cells and tissues provides a new tool to investigate signal transduction mechanisms, including calcium signaling, by modulating intracellular release and capacitative calcium entry through receptors in the plasma membrane.

The studies on nsPEF effects on the release of internal calcium and activation of calcium influx in HL-60 cells are described below.

Materials and Methods

Cell culture—Non-transformed HL-60 cells were used for this study and were obtained from American Type Culture Collection (ATCC, Rockville, Md.). They were cultured in 75-cm flasks in phenol-red RPMI 1640 (Mediatech Cellgro, Va.) supplemented with 20% fetal bovine serum (Atlanta Biologicals, Norcross, Ga.), 1% L-glutamine and 1% penicillin streptomycin (Mediatech Cellgro, Va.) and incubated at 37° C. with 5% $CO_2$. HL-60 cells in log-phase were removed from culture and re-suspended in a physiological buffer containing 145 mM NaCl, 5 mM KCl, 0.4 mM $NaH_2PO_4$, 1 mM $MgSO_4 \cdot 7H_2O$, 6 mM glucose, 5 mM HEPES (pH 7.4) prior to experimentation. 2 mM $CaCl_2$ was added to this buffer when loading cells with fluorescent indicators unless otherwise stated. In some experiments extracellular calcium was omitted by washing the cells several times in the same physiological buffer without added calcium.

Administration of nsPEF—Cell suspension ($7.7 \times 10^6$ cells/ml) was added into the BioRad gene Pulser® cuvettes (Bio-Rad Laboratories, Hercules, Calif.) prior to nsPEF pulsing. nsPEF was delivered by means of a cable pulse generator to a cuvette with two parallel plate electrodes separated by 0.4 cm containing cell suspensions. The generator consisted of a 10 Ω pulse-forming network (PFN) (five 50Ω cables in parallel) and a spark gap in atmospheric air as a nanosecond closing switch (Beebe, S. J., et al. (2003) *FASEB J.* 17, 1493-1495). Post pulse, the cell suspension was removed from the pulsing cuvette and assayed.

Microscopic Analysis of Internal Calcium Response—An Olympus photomicroscope with a Kodak DC-120 digital camera was used with the fluorescent indicator fluo-3 (Molecular Probes, Eugene, Oreg.) to assess changes in intracellular free calcium. HL-60 cells were suspended in the above described physiological buffer containing 2 mM calcium. Fluo-3/AM (2 μM) was added to the cells and the cells were then incubated at 37° C. for 45 minutes. The cells were then washed and re-suspended in the physiological buffer with or without 2 mM calcium. An aliquot of HL-60 cell suspension was loaded into a space between metal electrodes affixed to a pulsing slide for real-time monitoring of calcium transients. A description of this pulsing apparatus can be found in Deng et al. (2003) *Biophys. J.* 84, 2709-2714. To analyze the cell response, Merlin software (Life Sciences Resources) was used to detect changes in grey scale of the selected cell areas and compared these changes to a background region.

Assessment of Membrane Integrity—Propidium iodide (PI) (Molecular Probes, Eugene, Oreg.), at a final concentration of 10 μg/ml, was added to HL-60 cell suspension (7.7× $10^6$ cells/ml) in a 0.4 cm pulsing cuvette. For each of the four electric field settings, the cells were given one 60 ns pulse. Immediately following nsPEF stimulation, the cells were then removed from the cuvettes and transferred to flow cytometry vials for analysis (CellQuest software) on a FACSCalibur flow cytometer (Becton Dickinson). As a positive control, 0.1% Triton was added to cells to induce membrane disruption in the presence of PI. The cell suspensions were analyzed within 2 minutes of pulsing.

Fluorometric Analysis of Internal Calcium Response—To analyze the response of a greater number of cells, the fluorescent indicator fura-2 (Molecular Probes, Eugene, Oreg.) was used with a fluorometer. HL-60 cells were incubated with fura-2/AM (2 μM) in the physiological buffer described above containing 2 mM calcium for 45 minutes at 37° C. The cells were then washed and resuspended in calcium-free or calcium-containing buffer at a concentration of 7.7×$10^6$ cells/ml. Calcium measurements were performed in a SPEX ARCM spectrofluorometer, similar to that described previously (Dobrydneva Y., Blackmore, P. (2001) *Mol. Pharmcol.* 60, 541-552). Pulser® cuvettes could not be used to perform calcium measurements in the fluorometer because of the aluminum plates, which act to block either the excitation light or the emission light depending on the placement of the cuvette in the fluorometer. Therefore, the cells were first placed in the fluorometer cuvette, to obtain a baseline reading, cells were then removed from the fluorometer cuvette with a Pasteur pipette and added to the Pulser® cuvette. Cells were treated with nsPEF (Schoenbach, K. H., Beebe, S. J., and Buescher, E. S. (2001) *Bioelectromagnetics* 22, 440-448), then immediately removed from the Pulser® cuvette and added back to the fluorometer cuvette (located in close proximity to the pulse generator, which took between 5 and 10 seconds) and the fluorescence measurements continued. Preliminary experiments, using fiber optic light guides, to measure nsPEF effects, in the Pulser® cuvette in real-time with a fluorometer, showed increases in $[Ca^{2+}]_i$ similar to that seen with UTP. This type of analysis was not continued due to the high signal to noise ratio.

Results of Calcium Mobilization Experiments

Figure 4:
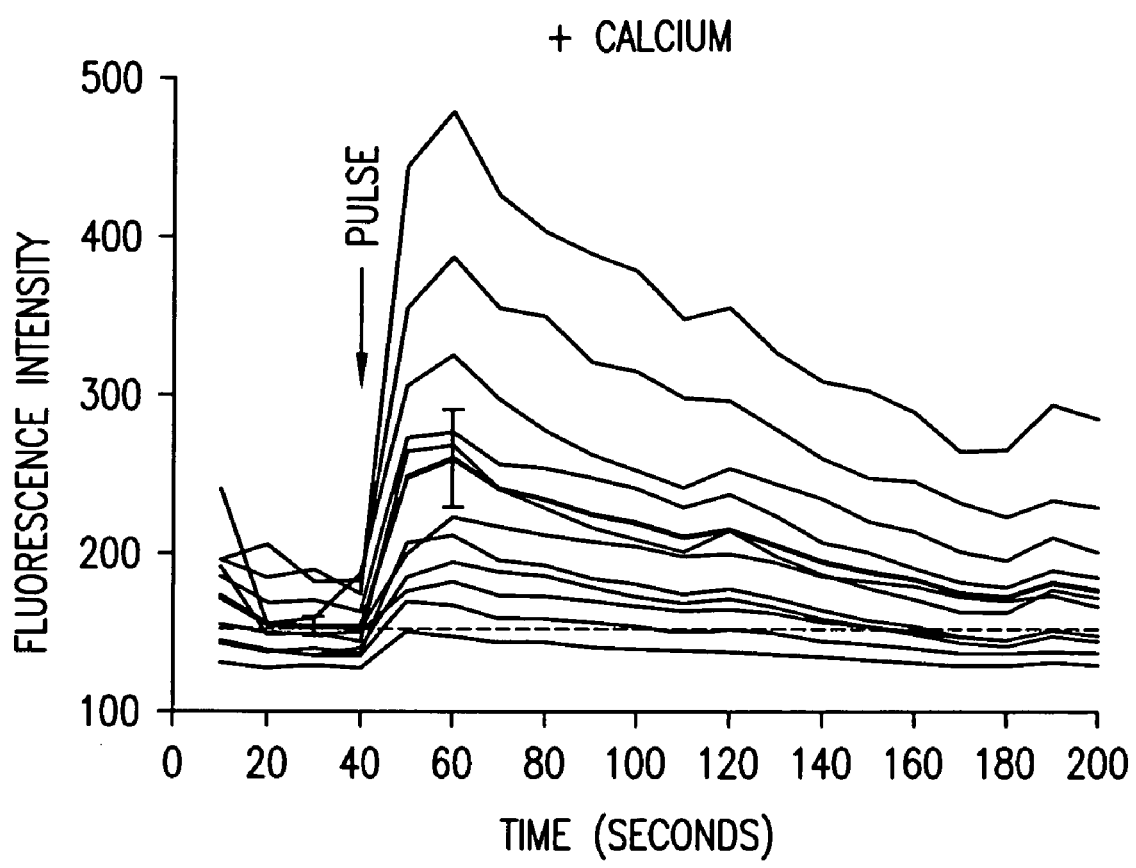
FIG. 4 describes how HL-60 cells respond to nsPEF treatment by increasing intracellular calcium. HL-60 cells, loaded with fluo-3 fluorescent indicator, in the presence of extracellular calcium, were stimulated with one 60 ns pulse (30 kV/cm) and analyzed in real-time. Images were taken as frames at 10 second intervals. Where an nsPEF pulse was administered, the majority of cells showed an increase in fluorescence compared to baseline (p-value 0.004). The average response of 22 untreated cells is shown as a dashed line with error bars representing S.E.M. Data is representative of 3 separate experiments.
Figure 5:
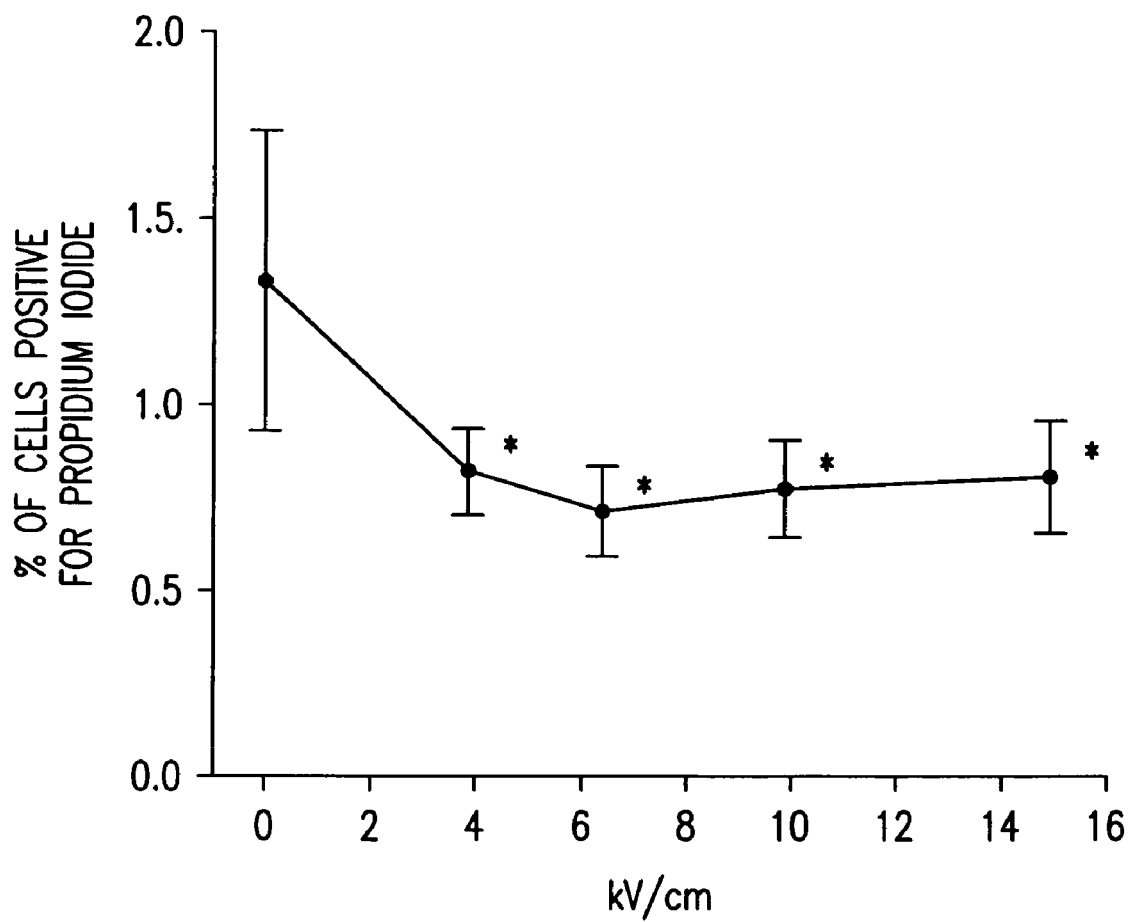
FIG. 5 exhibits HL-60 cells stimulated by nsPEF maintain plasma membrane integrity. Propidium iodide uptake in HL-60 cells due to nsPEF is expressed as a percentage of total cells gated. Compared to control (untreated cells) there is no significant uptake of PI in nsPEF treated HL-60 cells at the defined electric fields. Data analysis represents the mean of 3 experiments±S.E.M. *P-values for each condition: 4 kV/cm, 0.089; 6.5 kV/cm, 0.076; 10 kV/cm, 0.11; 15 kV/cm, 0.15.
Figure 6:
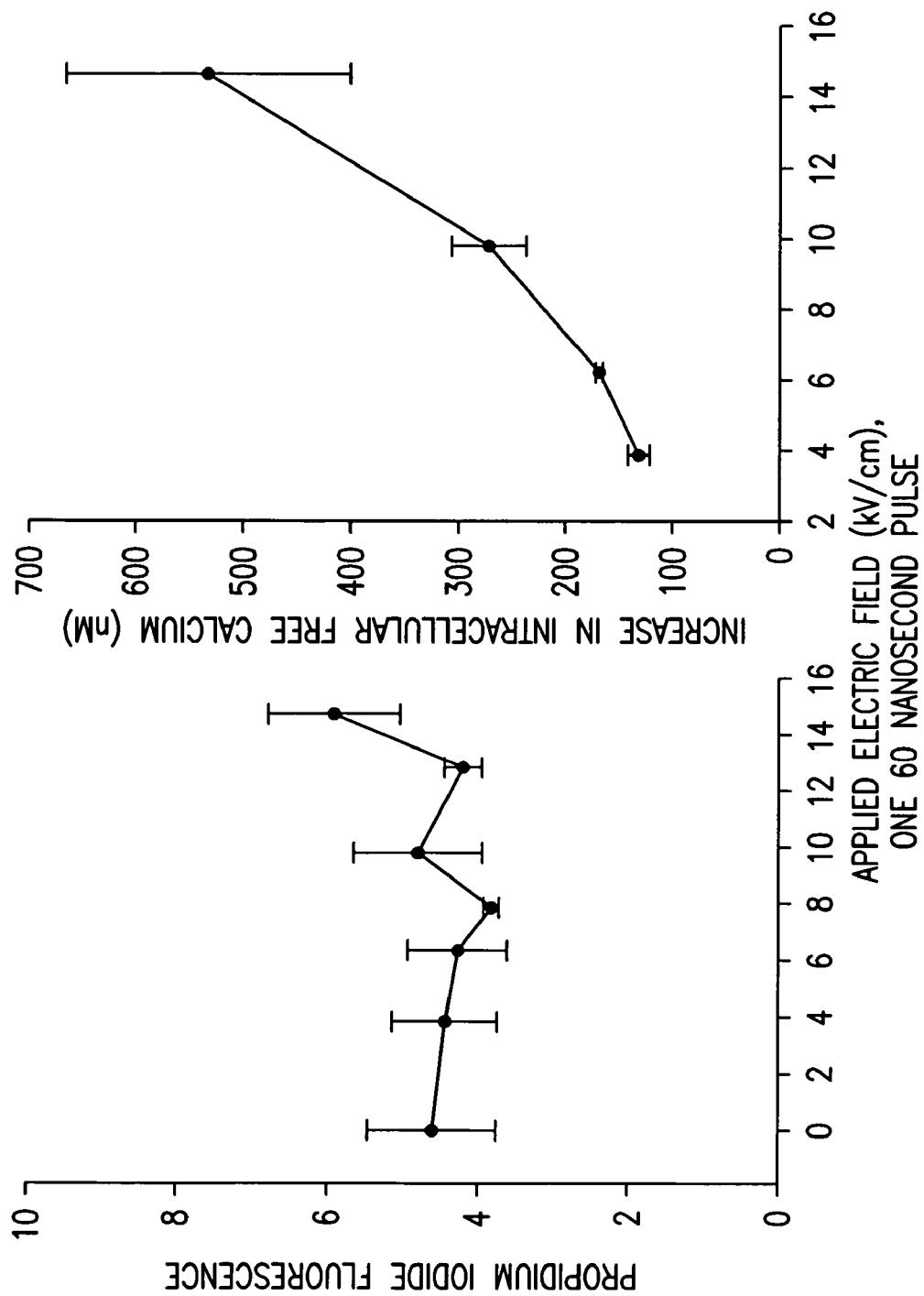
FIG. 6 shows that nsPEFs increase intracellular calcium while maintaining plasma membrane integrity. In the left panel, HL-60 cells were pulsed with a single nsPEF at various electric fields in the presence of propidium iodide, a marker for plasma membrane integrity. No significant increase in propidium iodide was observed indicating that the plasma membrane remained intact. In the right panel intracellular calcium was measured using fura-2 fluorescence in the presence of extracellular calcium. There was an electric field dependent increase in calcium mobilization in response to nsPEFs.

Single cell analysis of the effect of nsPEF on intracellular free calcium. In order to assess how nsPEF stimulation affects internal events in cells, real-time microscopic analysis of cells with the fluorescent calcium indicator fluo-3 was utilized. HL-60 cell suspension was loaded into the pulsing slide (Deng, J., Schoenbach, K. H., Buescher, E. S., Hair, P. S., Fox, P. M., Beebe, S. J. (2003) *Biophys. J.* 84, 2709-2714), and a group of cells in the field of vision between the electrodes was chosen to analyze. Typically 10-15 cells could be viewed at one time and their response to nsPEF recorded. All cells that were present in the microscope field of view were analyzed for changes in internal calcium. In FIG. 4, each cell in the microscope's field of view is represented as an individual line and the average response presented as a bold line. The fluorescence of each cell was monitored over the time of the experiment and compared to background. Following the nsPEF pulse (referenced by a black arrow) all of the cells responded with an increase in $[Ca^{2+}]_i$. This coordinated increase in $[Ca^{2+}]_i$ was not seen in untreated cells. This increase in $[Ca^{2+}]_i$ following nsPEF could result from intracellular calcium mobilization followed by CCE.

nsPEF does not induce electroporation of the plasma membrane at low electric fields. It was important to determine that the increase in $[Ca^{2+}]_i$ (FIG. 4) was not due to electroporation of the plasma membrane which would allow calcium influx from the media. Classical electroporation experiments use applied electric fields of sufficient duration to induce dielectric breakdown in the plasma membrane (Tsong, T. Y. (1991) *Biophys J.* 60, 297-306; Grinstein S., Furuya W. (1988) *J. Biol. Chem.* 263, 1779-1783), therefore plasma membrane integrity was assessed under the experimental conditions used in this study using PI with flow cytometry. In each experiment, a cell suspension was loaded into a pulsing cuvette and given one, 60 ns pulse. This was repeated for 4 electric field settings, as shown in FIG. 5. The data revealed a small decrease in PI uptake that was not significant when compared to control. In all subsequent experiments, in this study, cells were treated within this electric field range to ensure membrane integrity.

Figure 7:
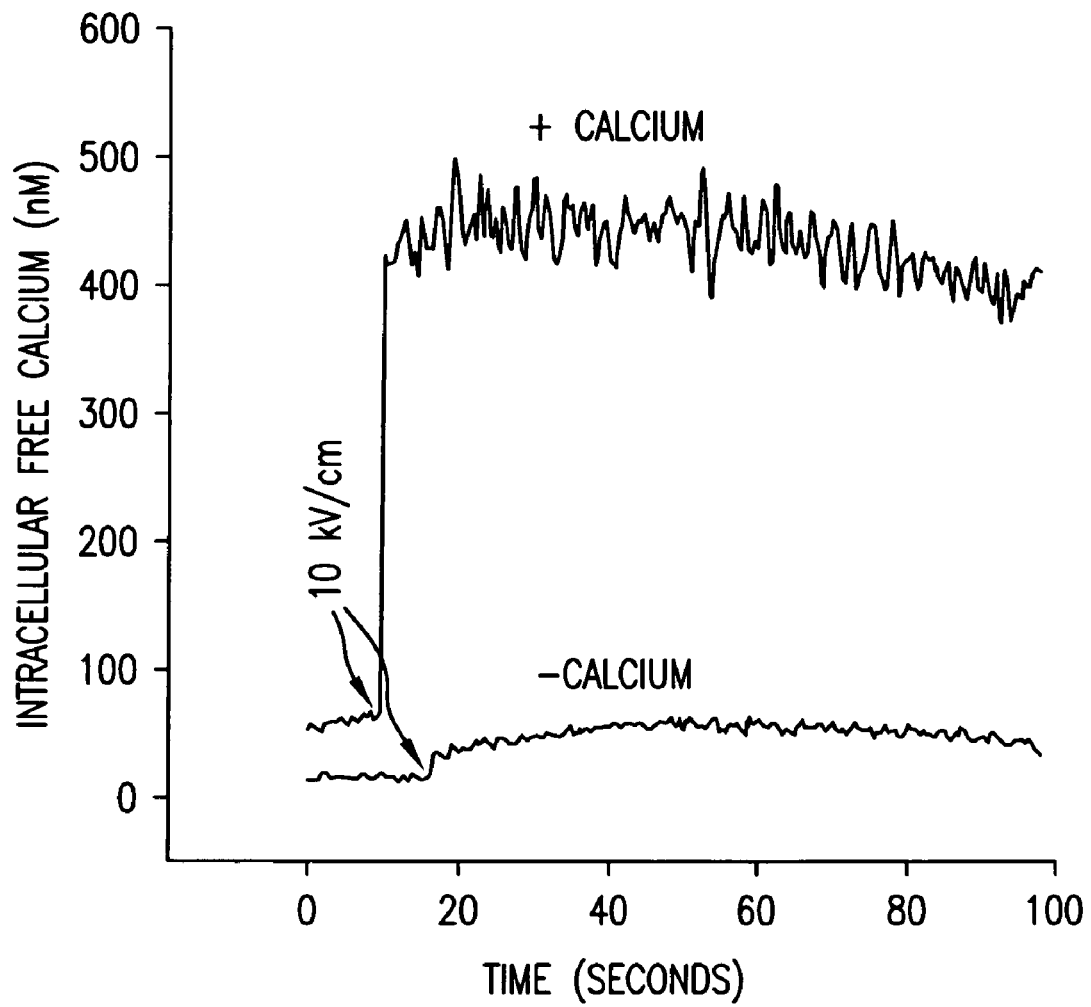
FIG. 7 exhibits the effects of one 60 ns pulse at 10 kV/cm, 10 µM UTP, and 0.1 µM thapsigargin on $[Ca^{2+}]_i$ in fura-2 loaded HL-60 cells incubated with and without extracellular calcium. HL-60 cells (incubated with and without extracellular calcium) were placed in the fluorometer cuvette to obtain a baseline $[Ca^{2+}]_i$ value then removed into the BioRad Gene Pulser® cuvette. The cells were pulsed for 60 ns at 10 kV/cm, then removed back into the fluorometer cuvette and $[Ca^{2+}]_i$ was again measured.
Figure 8:
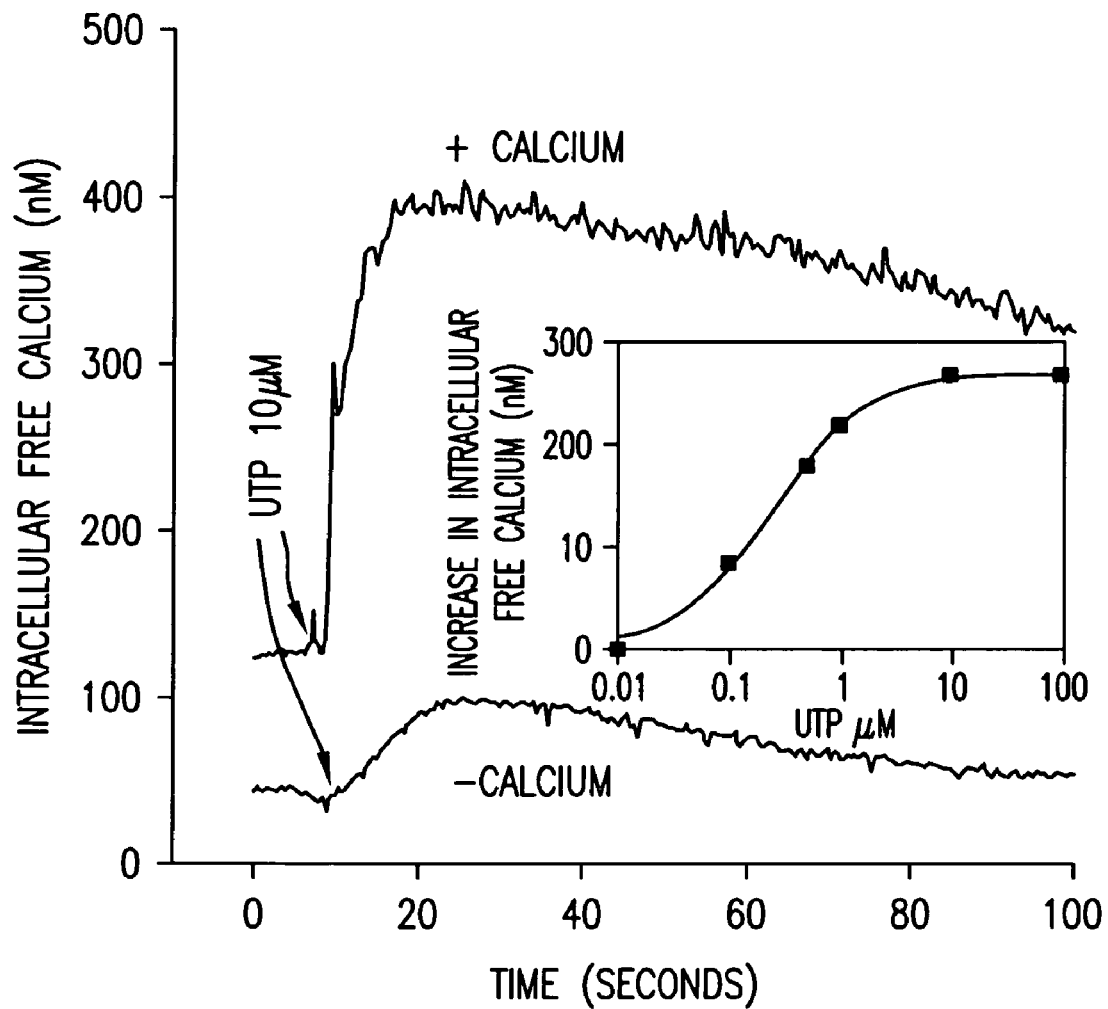
FIG. 8 shows the effect of 10 µM UTP on $[Ca^{2+}]_i$ measured in HL-60 cells in the presence and absence of extracellular calcium. Shown in the FIG. 8 insert is a dose response curve of UTP to increase $[Ca^{2+}]_i$ in HL-60 cells in the presence of extracellular calcium. Various concentrations of UTP were added to fura-2 loaded cells at 15 seconds and the $[Ca^{2+}]_i$ calcium measured.
Figure 9:
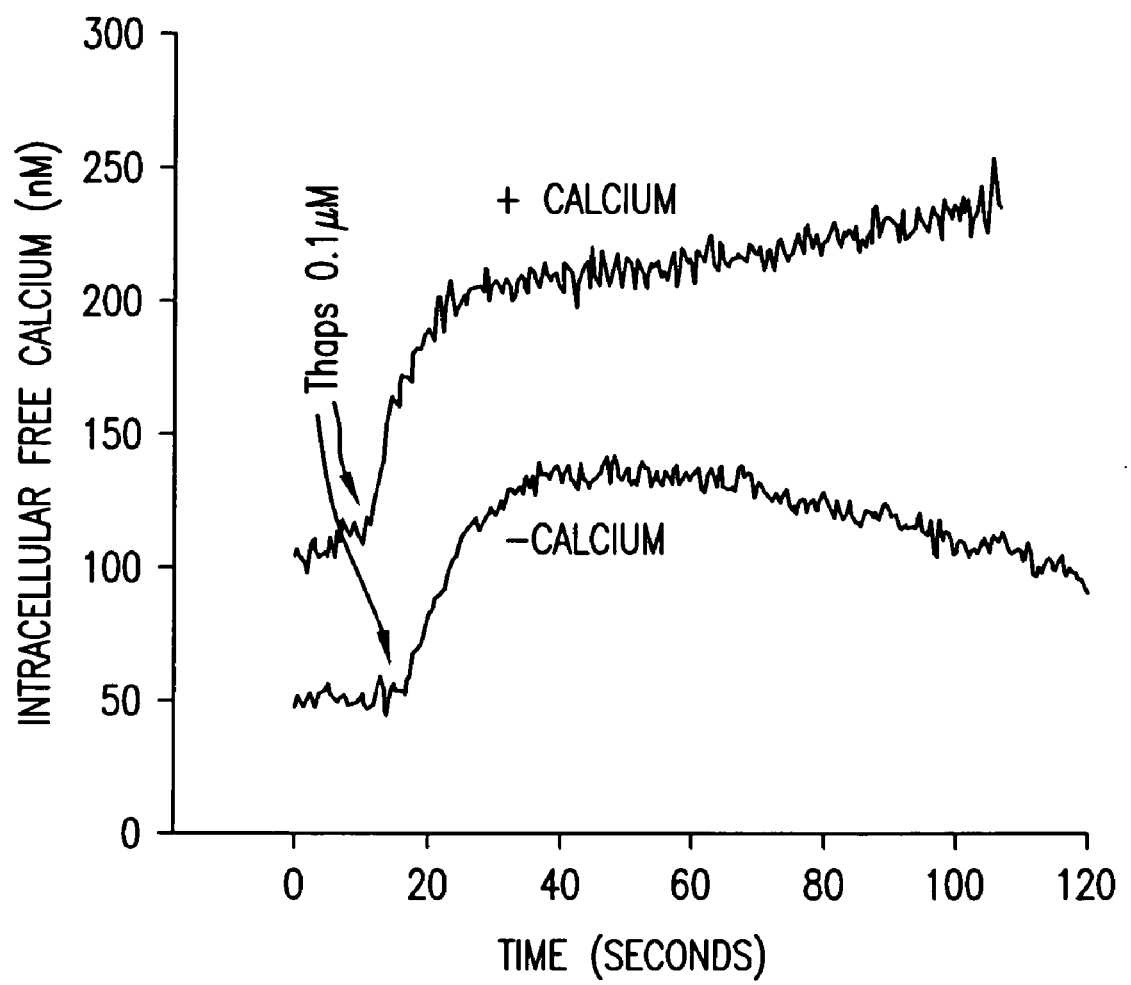
FIG. 9 shows the effect 0.1 µM thapsigargin on $[Ca^{2+}]_i$ measured in HL-60 cells in the presence and absence of extracellular calcium. Representative traces of at least 3 experiments are shown.

Effect of single nsPEF pulses and traditional agonists on HL-60 cells. The amount of calcium released from internal stores and that which entered from the external media was then evaluated using the fluorescent indicator fura-2, which permits $[Ca^{2+}]_i$ to be quantified. These measurements of the response to nsPEF and other agonists could then be compared. The data in FIG. 7 shows a typical result when cells were pulsed once at 10 kV/cm for 60 ns. In the presence of extracellular calcium there was a rapid and sustained increase in $[Ca^{2+}]_i$ of approximately 400 nM, which gradually declined with time. In the absence of extracellular calcium the basal $[Ca^{2+}]_i$ was lower than when extracellular calcium was present suggesting that HL-60 cells are not able to completely maintain internal calcium levels in a calcium deficient environments. One 10 kV/cm pulse for 60 ns in the absence of extracellular calcium gradually increased $[Ca^{2+}]_i$ by approximately 40 nM, which then slowly declined after approximately 30 seconds. Since this result is similar to agonist-induced increases in $[Ca^{2+}]_i$ in many different cell types, HL-60 cells were challenged with a known agonist that increased $[Ca^{2+}]_i$. UTP was chosen since this has been used previously to elevate $[Ca^{2+}]_i$ in HL-60 cells (Tsong, T. Y. (1991) *Biophys J.* 60, 297-306). The data in FIG. 8 shows that 10 μM UTP increased $[Ca^{2+}]_i$ by approximately 300 nM when extracellular calcium was present. This agonist, at 10 μM, produced a rapid and sustained increase in $[Ca^{2+}]_i$ that was of a similar magnitude and duration to that observed with the one 60 ns 10 kV/cm pulse. A 100 μM concentration of UTP did not produce any larger effect on $[Ca2+]_i$, while 0.1 M UTP produced an effect on $[Ca^{2+}]_i$ that was approximately 20% of that seen with 10 μM UTP, thus UTP produced a dose dependent effect on $[Ca^{2+}]_i$ (FIG. 8 insert). Similar results were obtained using ATP as an agonist. In the absence of extracellular calcium UTP increased $[Ca^{2+}]_i$ by approximately 50 nM, and the increase in $[Ca^{2+}]_i$ was transient, consistent with intracellular calcium stores being depleted. Since it is believed that purinergic stimulation of HL-60 cells results in an increase $[Ca^{2+}]_i$ via intracellular calcium mobilization, followed by activation of store-operated calcium channels in the plasma membrane, thapsigargin was utilized to examine whether or not HL-60 cells possess a store-operated calcium mechanism. The data in FIG. 9 shows that thapsigargin produced a prolonged increase in $[Ca^{2+}]_i$ when extracellular calcium was present and a smaller and more transient increase in $[Ca^{2+}]_i$ when extracellular calcium was absent. These results are consistent with 60 ns pulses producing an increase in $[Ca^{2+}]_i$ that is comparable to that seen with UTP and thapsigargin and that a store mediated calcium entry process is involved.

Figure 10:
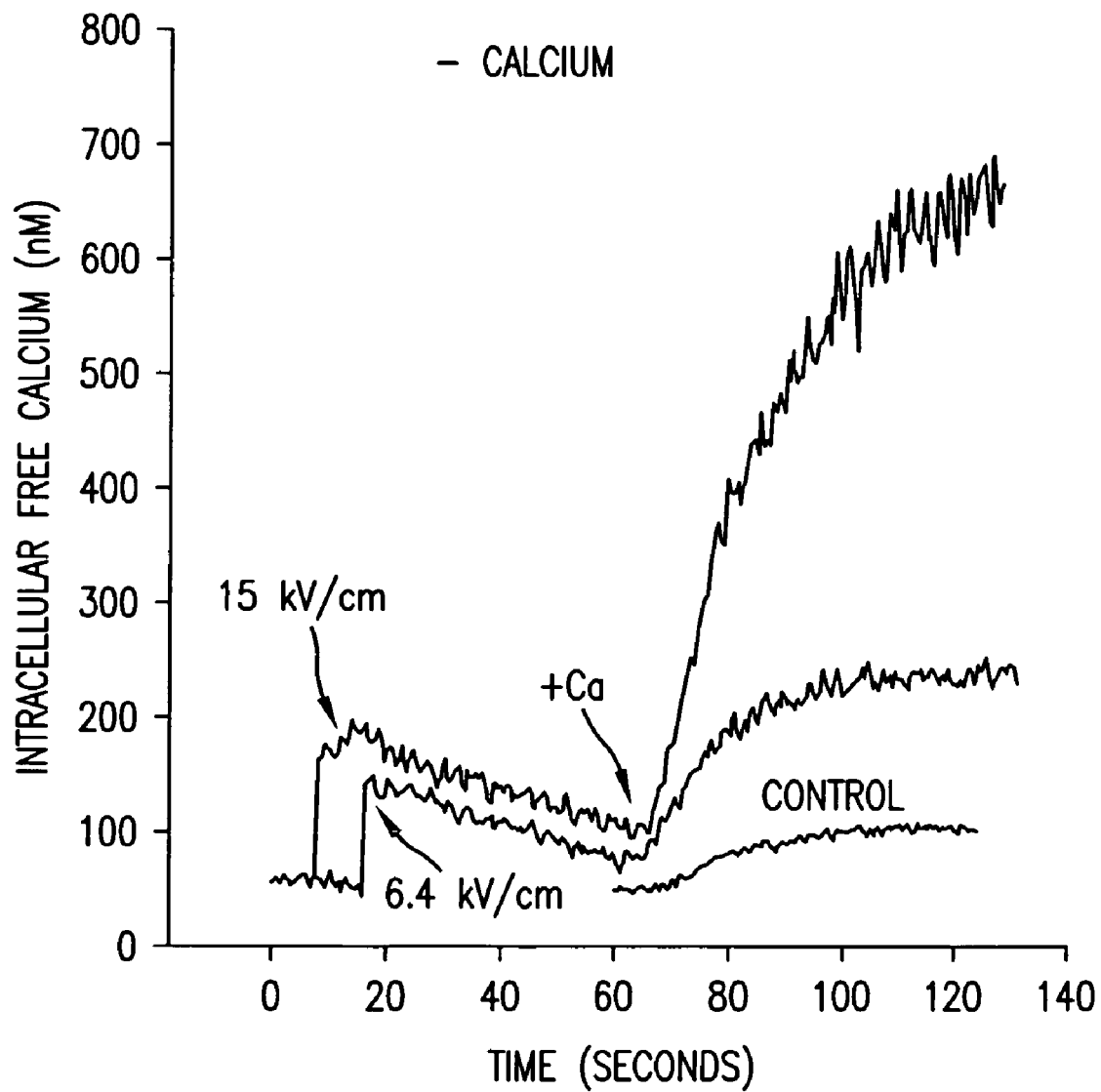
FIG. 10 shows capacitative calcium entry into HL-60 cells treated with one 60 ns pulse each of 6.4 kV/cm or 15 kV/cm and cells treated with UTP. HL-60 cells were incubated in the absence of extracellular calcium. Cells, incubated in calcium-deficient media, were treated with one 60 ns pulse at 6.4 kV/cm or 15 kV/cm. After $[Ca^{2+}]_i$ had returned to near basal values, 1.0 mM calcium was added to the cells. Untreated cells acted as a control and show that some basal calcium influx occurred in this calcium deficient situation.
Figure 11:
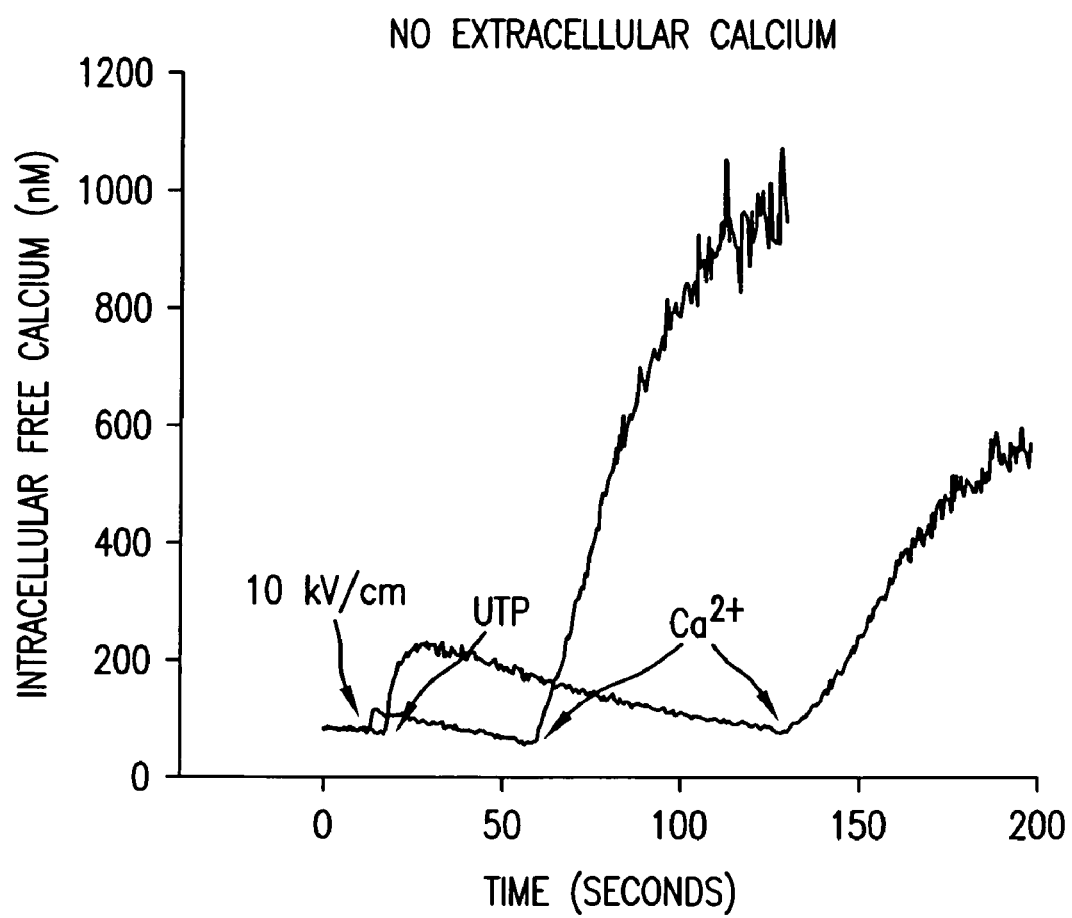
FIG. 11 shows how purinergic agonists and nsPEFs release calcium from the endoplasmic reticulum and activate store-operated channels in the plasma membrane. HL-60 cells were treated with one 60 ns pulse each of 10 kV/cm and cells were then treated with UTP. HL-60 cells were incubated in the absence of extracellular calcium. Cells, incubated in calcium-deficient media, were treated with one 60 ns pulse at 10 kV/cm. After $[Ca^{2+}]_i$ had returned to near basal values, 1.0 mM calcium was added to the cells.
Figure 12:
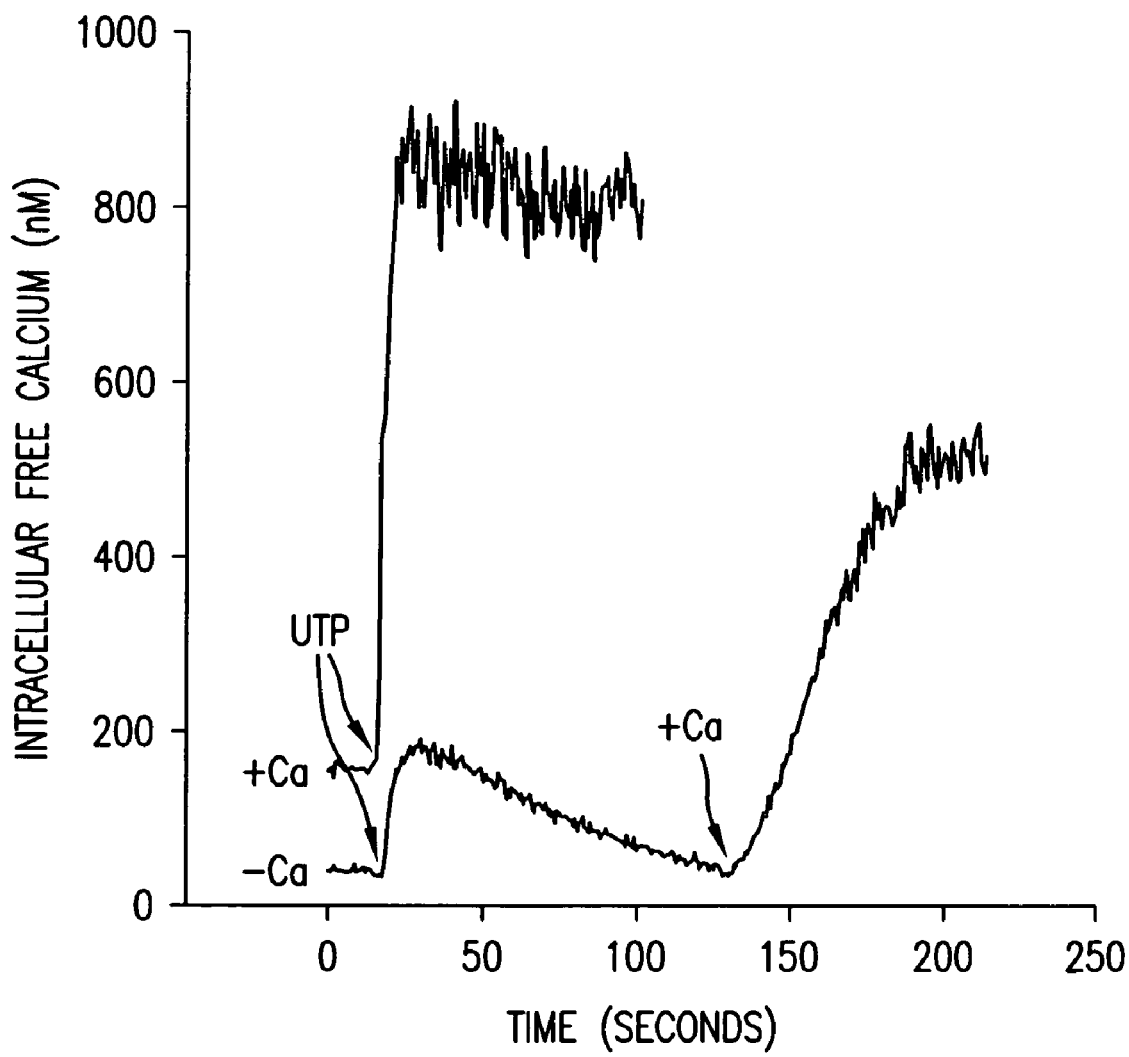
FIG. 12 shows cells that were treated with 10 µM UTP and, when $[Ca^{2+}]_i$ had returned to basal values, 1.0 mM calcium was added. The increase in $[Ca^{2+}]_i$ was similar to that observed when cells were given UTP in the presence of extracellular calcium. Representative traces of at least 3 experiments are shown.

Evidence of capacitative calcium entry activation in HL-60 cells. In order to evaluate the activity of CCE, HL-60 cells were treated with nsPEF in calcium-deficient media and the response of the cells to calcium re-introduction was monitored. The data in FIG. 10 shows that when cells were pulsed for 60 ns with an amplitude of 6.4 or 15 kV/cm in calcium-deficient media, there was a small and transient increase in $[Ca^{2+}]_i$ consistent with the data shown in FIG. 7. The 15 kV/cm pulse produced a larger increase in $[Ca^{2+}]_i$ than that seen with the 6.4 kV/cm pulse. When calcium was added to the cells that had been pulsed, there was a rapid rise in $[Ca^{2+}]_i$ consistent with calcium influx channels being activated. The increase in $[Ca^{2+}]_i$ was dependent on the electric field intensity of the pulse since the 15 kV/cm pulse produced a larger increase in $[Ca^{2+}]_i$ than the 6.4 kV/cm pulse, and these increases in $[Ca^{2+}]_i$ were greater than the increase in $[Ca^{2+}]_i$ seen in control (untreated) cells. It was determined that there exists a dose dependent response of increasing $[Ca^{2+}]_i$ with increasing electric fields. The data in FIG. 12 shows that the effect of UTP on $[Ca^{2+}]_i$ is small and transient in low calcium-containing buffer, consistent with the data shown in FIG. 8. The addition of 1.0 mM calcium to these UTP treated cells produced a rapid rise in $[Ca^{2+}]_i$ that was comparable to that observed when cells were treated with UTP in calcium-containing media. (FIG. 8). Since UTP has been previously shown to promote capacitative calcium entry in HL-60 cells, the data shown in FIG. 12 was entirely consistent with this process. The results in FIG. 10 show that pulsing of HL-60 cells promotes a stimulation of calcium entry similar to that seen following UTP stimulation implying that pulsing was also promoting capacitative calcium entry.

Figure 13:
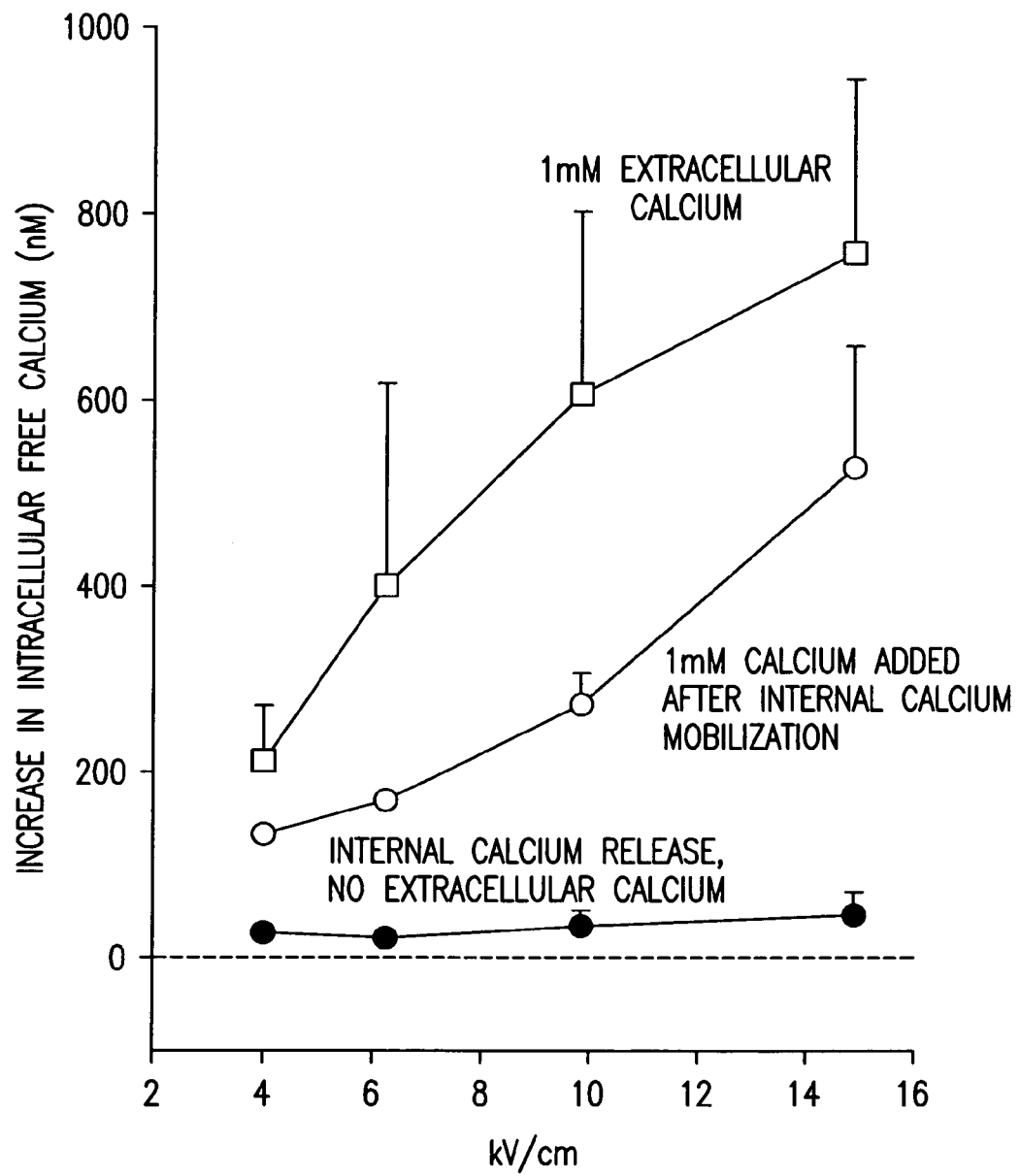
FIG. 13 exhibits the effects of one 60 ns pulse each of 4.0, 6.4, 10.0 or 15.0 kV/cm on $[Ca^{2+}]_i$ in HL-60 cells. The three conditions described are: (□) when 1 mM extracellular calcium was present, (●) in the absence of extracellular calcium and (○) when 1 mM calcium was added to cells after stimulation in the absence of extracellular calcium. Data represent the mean±S.E.M. from three separate experiments.

Dose dependent increase in $[Ca^{2+}]_i$ and CCE to nsPEF. In order to evaluate the electric field dependence of increasing $[Ca^{2+}]_i$ and CCE with nsPEF HL-60 cells were treated with nsPEF at varying electric fields. The data in FIG. 13 shows the effect of one 60 ns pulse at various electric field settings, in the presence and absence of extracellular calcium, and the effect of adding extracellular calcium on $[Ca^{2+}]_i$ after stimulation without calcium as a measure of CCE. With calcium present in the extracellular medium, nsPEF induced an electric field-dependent increase in $[Ca\ 2+]_i$. The maximum effect on $[Ca^{2+}]_i$ was approximately 800 nM with one pulse at 15 kV/cm. Increasing the number of pulses to three, five and ten, separated by approximately one second intervals, did not produce any larger effect on $[Ca^{2+}]_i$ than a single 15 kV/cm pulse. However, at lower electric fields increasing the pulse number caused additional increases in intracellular calcium, but not above levels induced by 15 kV/cm. An effect of nsPEF on intracellular mobilization was observed (FIG. 13 solid circles), however the maximum effect on $[Ca^{2+}]_i$ was approximately 50 nM, this effect was much less than that observed when calcium was present in the medium. However, when calcium was added to these stimulated cells (FIG. 13 open circles), there was an electric field-dependent rapid rise in $[Ca^{2+}]_i$ that approached values similar to those seen when calcium was present during stimulation (FIG. 13 open squares). Now that it has been determined that HL-60 cells respond to nsPEF in an lectric field-dependent manner, whether the nsPEF treatment was depleting the same intracellular stores as UTP was assessed.

Figure 14:
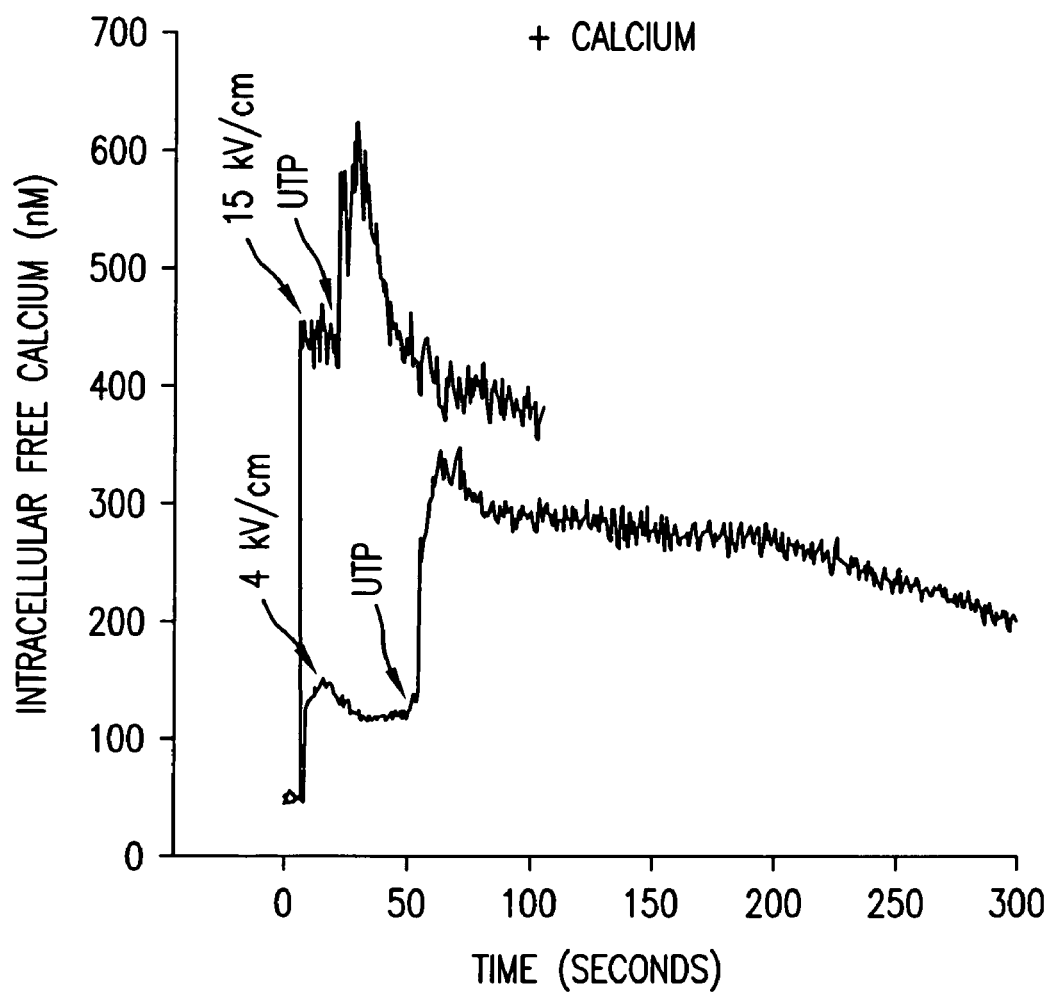
FIG. 14 exhibits the effects of UTP on $[Ca^{2+}]_i$ after one 60 ns pulse each of 4 kV/cm or 15 kV/cm. Fura-2 loaded HL-60 cells were incubated in calcium-containing media. Cells were either pulsed at 15 kV/cm or 4 kV/cm. Shortly after pulsing, the increase in $[Ca^{2+}]_i$ was measured and 10 μM UTP was then added. Representative traces are shown.

Effect on $[Ca^{2+}]_i$ in HL-60 cells following sequential stimulation with UTP and nsPEF. The data in FIG. 14 shows the pulse dependent nature of the increase in $[Ca^{2+}]_i$, with the 15 kV/cm pulse producing an effect approximately 4 times larger than the effect seen with 4 kV/cm. The data in FIG. 13 indicated that the pulsing of HL-60 cells was promoting intracellular calcium mobilization and calcium influx via a capacitative influx mechanism similar to the effect of UTP, an agent that also promotes capacitative calcium influx. Therefore it seemed logical that the increase in $[Ca^{2+}]_i$ induced by UTP would be influenced by prior pulsing if nsPEFs and UTP were sharing the same capacitative mechanism. When cells were pulsed with 15 kV/cm, the subsequent effect of UTP to increase $[Ca^{2+}]_i$ was greatly reduced and although there was a very rapid increase in $[Ca\ 2+]_i$ the effect on $[Ca^{2+}]_i$ was very transient. When cells were pulsed at 4 kV/cm, which produced a smaller increase in $[Ca^{2+}]_i$, the subsequent UTP challenge produced a rapid increase in $[Ca^{2+}]_i$ that was more prolonged in nature. This is similar to the effect seen without prior pulsing (FIG. 8). Thus the effect of UTP to increase $[Ca^{2+}]_i$ was inversely proportional to the electric field intensity of the pulse. This data suggests that nsPEF treatment and UTP target the same intracellular calcium pools.

Figure 15:
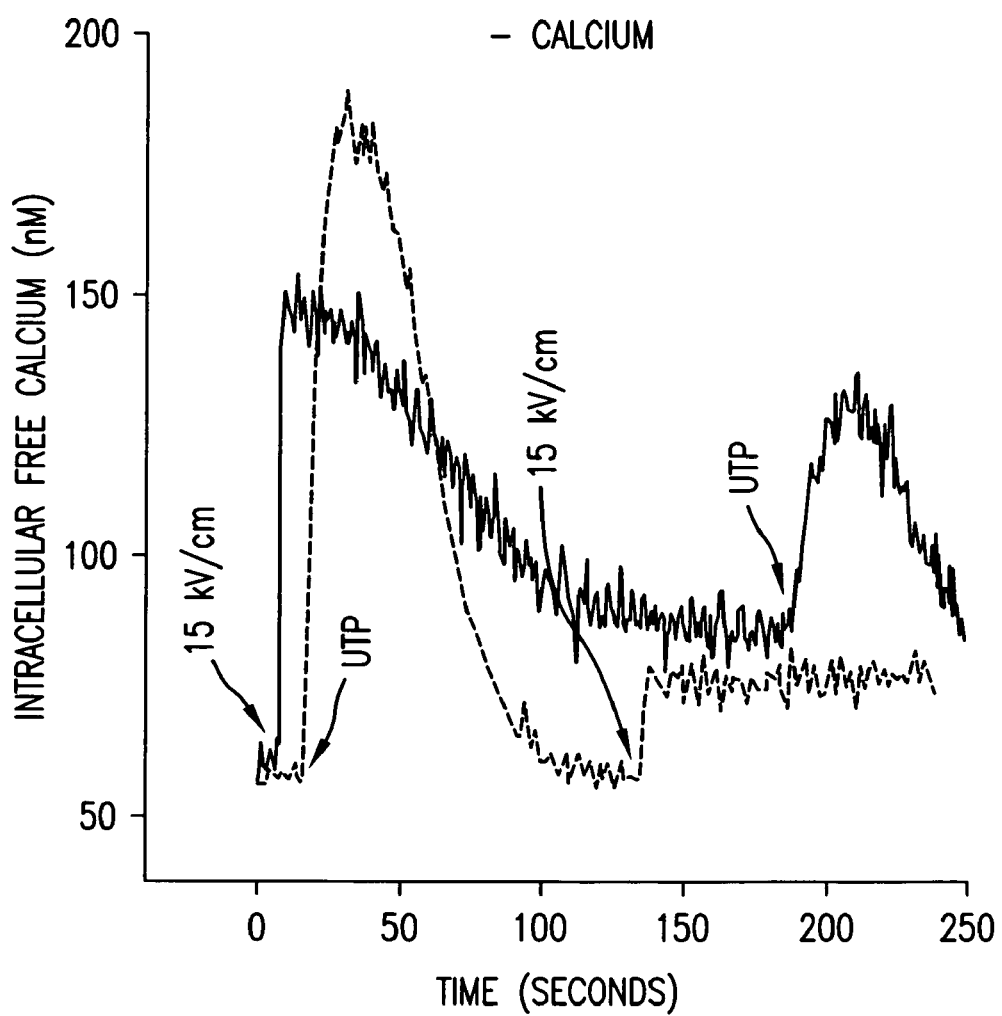
FIG. 15 shows the effects of one 60 ns 15 kV/cm pulse followed by 10 μM UTP, and the effect of 10 μM UTP followed by one 60 ns 15 kV/cm pulse on $[Ca^{2+}]_i$ in HL-60 cells incubated in calcium-deficient media and in the presence of 2 mM extracellular calcium. Both the 15 kV/cm pulse and UTP produced a transient increase in $[Ca^{2+}]_i$. The addition of UTP to the 15 kV/cm pulsed cells produced an effect on $[Ca^{2+}]_i$ that was less than that observed when UTP was added alone. Stimulating the cells with one 15 kV/cm pulse after UTP stimulation also produced an effect on $[Ca^{2+}]_i$ that was less than that seen with a pulse alone.

In order to more firmly support this hypothesis, the responses of these same type of experiments in the presence of calcium were compared with those in media deficient of calcium. The data in FIG. 15 shows the effect of one 15 kV/cm pulse on $[Ca^{2+}]_i$ followed by stimulation with UTP and the effect of UTP stimulation on $[Ca^{2+}]_i$ followed by one 15 kV/cm pulse, when extracellular calcium was deficient. One 15 kV/cm pulse produced an increase of approximately 80 nM, which rapidly declined to a value just above the pre-stimulated level, and at this point (180 seconds) 10 µM UTP was added. The effect of UTP to increase $[Ca^{2+}]_i$ was much smaller (peak effect reduced by approximately 60%) to that observed when UTP was added before a pulse. Thus one pulse appeared to partially deplete the same pool of intracellular calcium that UTP was mobilizing, and this pool, based on the known signaling pathway for UTP in HL-60 cells, was the endoplasmic reticulum. The reverse protocol in which cells were challenged first with UTP then pulsed was also employed. UTP produced a transient increase in $[Ca^{2+}]_i$, consistent with UTP mobilizing calcium from the endoplasmic reticulum. Following this mobilization by UTP, cells were stimulated with one 15 kV/cm pulse. This pulse produced a small increase in $[Ca^{2+}]_i$ that was approximately 25% of that produced when cells were pulsed before UTP addition. This experiment is therefore consistent with the notion that nsPEF and UTP were mobilizing calcium from the same intracellular pool, which is most likely the endoplasmic reticulum.

Figure 16:
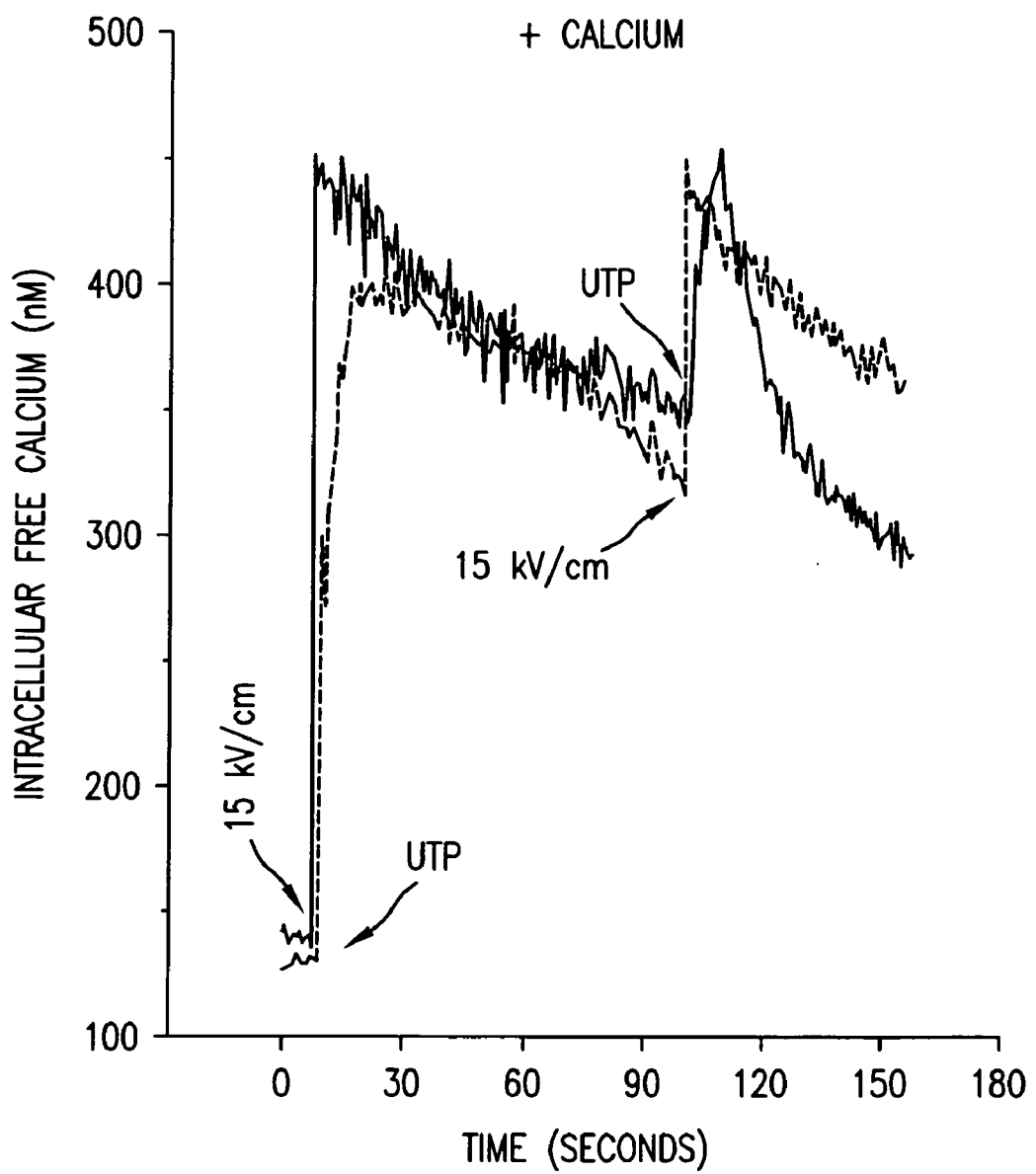
FIG. 16 shows that both the 15 kV/cm pulse and UTP produced rapid and sustained increases in $[Ca^{2+}]_i$. The addition of UTP to the 15 kV/cm pulsed cells produced an effect on $[Ca^{2+}]_i$ that was less than that observed when UTP was added alone to the cells. Stimulating the cells with one 60 ns pulse after UTP stimulation also produced an effect that was less than that observed with one pulse given alone. This heterologous desensitization suggests that both stimuli are mobilizing the same calcium pool. A representative experiment is shown.

The data in FIG. 16 shows the effect of one 15 kV/cm pulse on $[Ca^{2+}]_i$ followed by stimulation with UTP and the effect of UTP stimulation on $[Ca^{2+}]_i$ followed by one 15 kV/cm pulse, when extracellular calcium was present. In this experiment the elevation of $[Ca^{2+}]_i$ induced by pulsing and UTP was due to both intracellular calcium mobilization (FIG. 15) and calcium influx. The addition of UTP produced a rapid rise in $[Ca^{2+}]_i$ that was much larger than when there was no extracellular calcium present (FIG. 15), then it began to gradually decline. Cells were then pulsed at 15 kV/cm, which produced a rapid increase in $[Ca^{2+}]_i$, which was reduced by approximately 65% when compared to the effect observed before UTP stimulation. When cells were initially pulsed with 15 kV/cm a rapid rise in $[Ca^{2+}]_i$ was observed that was comparable to that observed with UTP stimulation by itself. Following this pulse, cells were stimulated with UTP. This effect of UTP was reduced by approximately 60% when compared to the effect of UTP by itself. Therefore, the fact that each previous stimulus reduced the effect of the subsequent stimulus is consistent with the theory that the same signaling pathway was being targeted. This is likely due to release of calcium from the endoplasmic reticulum.

Figure 17:
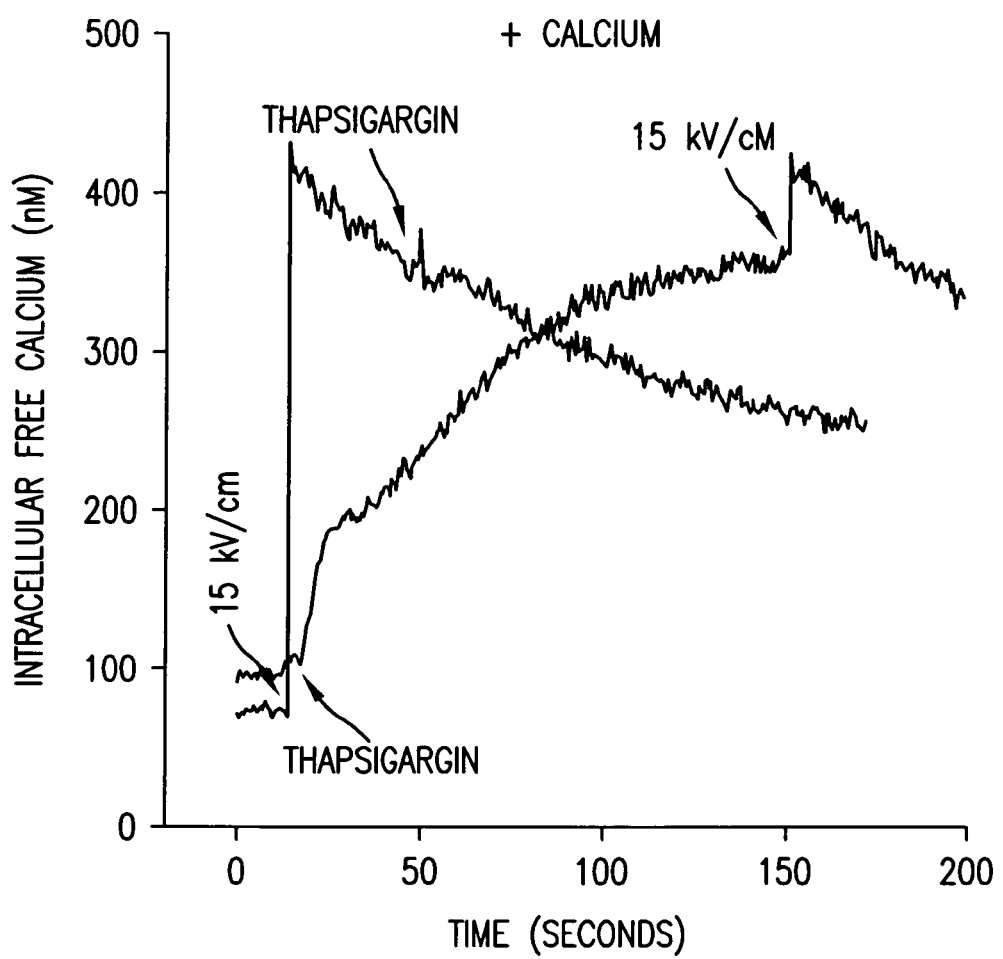
FIG. 17 describes the effects of one 60 ns 15 kV/cm pulse followed by 0.1 μM thapsigargin and the effect of 0.1 μM thapsigargin followed by one 60 ns 15 kV/cm pulse on $[Ca^{2+}]_i$ in HL-60 cells incubated in the presence of 1 mM extracellular calcium. The 15 kV/cm pulse produced a large increase in $[Ca^{2+}]_i$ that began to decline gradually; the addition of thapsigargin at 50 seconds did not increase $[Ca^{2+}]_i$ any further, since the $[Ca^{2+}]_i$ declined at the same rate as before thapsigargin addition. The addition of thapsigargin by itself produced a slow and sustained increase in $[Ca^{2+}]_i$, pulsing at 160 seconds with a 15 kV/cm pulse after thapsigargin produced a small and transient rise in $[Ca^{2+}]_i$. A representative experiment is shown.

The data in FIG. 10 and FIG. 13 support the concept that 60 ns pulsing initially mobilized intracellular calcium which then induced CCE. An agent that is commonly used to investigate CCE is thapsigargin (Treiman M., Caspersen C., Christensen S. B. (1998) *Trends Pharmacol. Sci.* 19, 131-135), which is a potent inhibitor of the sarco-endoplasmic reticulum $Ca^{2+}$-ATPases. Treatment of cells with thapsigargin promotes an emptying of the sarco-endoplasmic reticulum calcium stores with subsequent stimulation of CCE. The data in FIG. 17 shows that thapsigargin produced a gradual and sustained increase in $[Ca^{2+}]_i$. If pulsing depletes the sarco-endoplasmic reticulum of calcium, then it would be expected that pulsing after thapsigargin treatment would show a reduced release of calcium when compared to pulsing alone. The data in FIG. 17 shows that the effect of one 15 kV/cm pulse to increase $[Ca^{2+}]_i$ after thapsigargin treatment was reduced by approximately 85%. This result supports the notion that pulsing and thapsigargin are depleting the same calcium pool, which is believed to be the sarco-endoplasmic reticulum. The data in FIG. 17 also shows the converse experiment in which cells were first pulsed at 15 kV/cm and then challenged with thapsigargin. The one 15 kV/cm pulse increased $[Ca^{2+}]_i$ to approximately 400 nM which then began to gradually decline. At approximately 50 seconds electrically pulsed cells were challenged with thapsigargin, indicated by the arrow, however $[Ca^{2+}]_i$ did not increase, and in fact still gradually declined, thus indicating that pulsing had depleted the thapsigargin sensitive store of calcium which is the sarco-endoplasmic reticulum.

EXAMPLE 4

Figure 18:
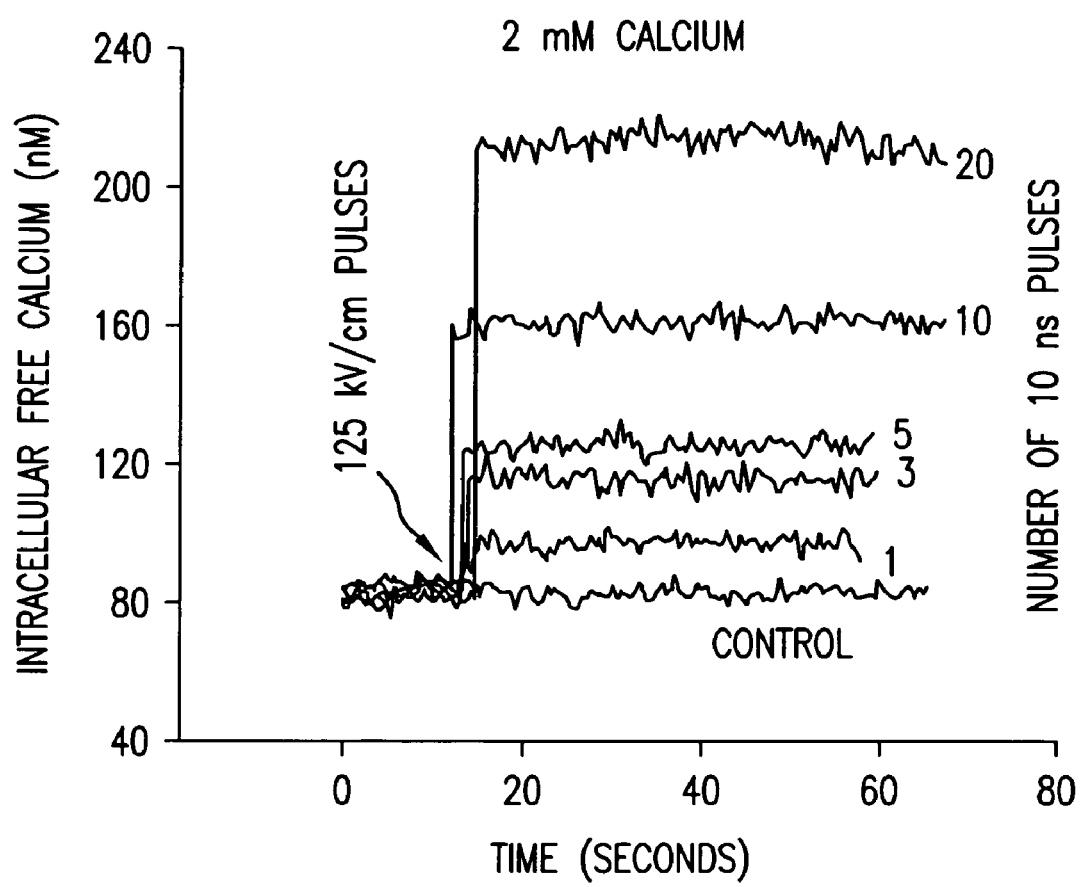
FIG. 18 shows the effects of nsPEF pulses (10 ns and 125 kV/cm) on intracellular free calcium in human platelets in the presence of calcium. Increases in intracellular calcium were shown to be dependent on the number of nsPEF pulses applied, with ten pulses cause a two-fold increase in calcium.

The Effect of nsPEFs in Increasing Intracellular Calcium in Human Platelets nsPEFs increase intracellular calcium in human platelets in a pulse-dependent manner, as shown in FIG. 18. nsPEF pulses (10 ns and 125 kV/cm) were applied to human platelets in experiments conducted in the presence of extracellular calcium. Calcium concentration was determined using Fura 2 as a quantifiable calcium indicator in a fluorometer. Increases in intracellular calcium were shown to be dependent on the pulse number (FIG. 18). Ten pulses caused a two-fold increase in calcium. The calcium response was also found to depend on the electric field condition. Specifically, longer pulses and lower electric fields (e.g. 60 ns and 30 kV/cm) produced more robust increases in calcium. Under these conditions, ten pulses caused a 3-fold increase in calcium. The kinetics of the calcium mobilization in response to nsPEF is different than the response to thrombin.

Figure 19:
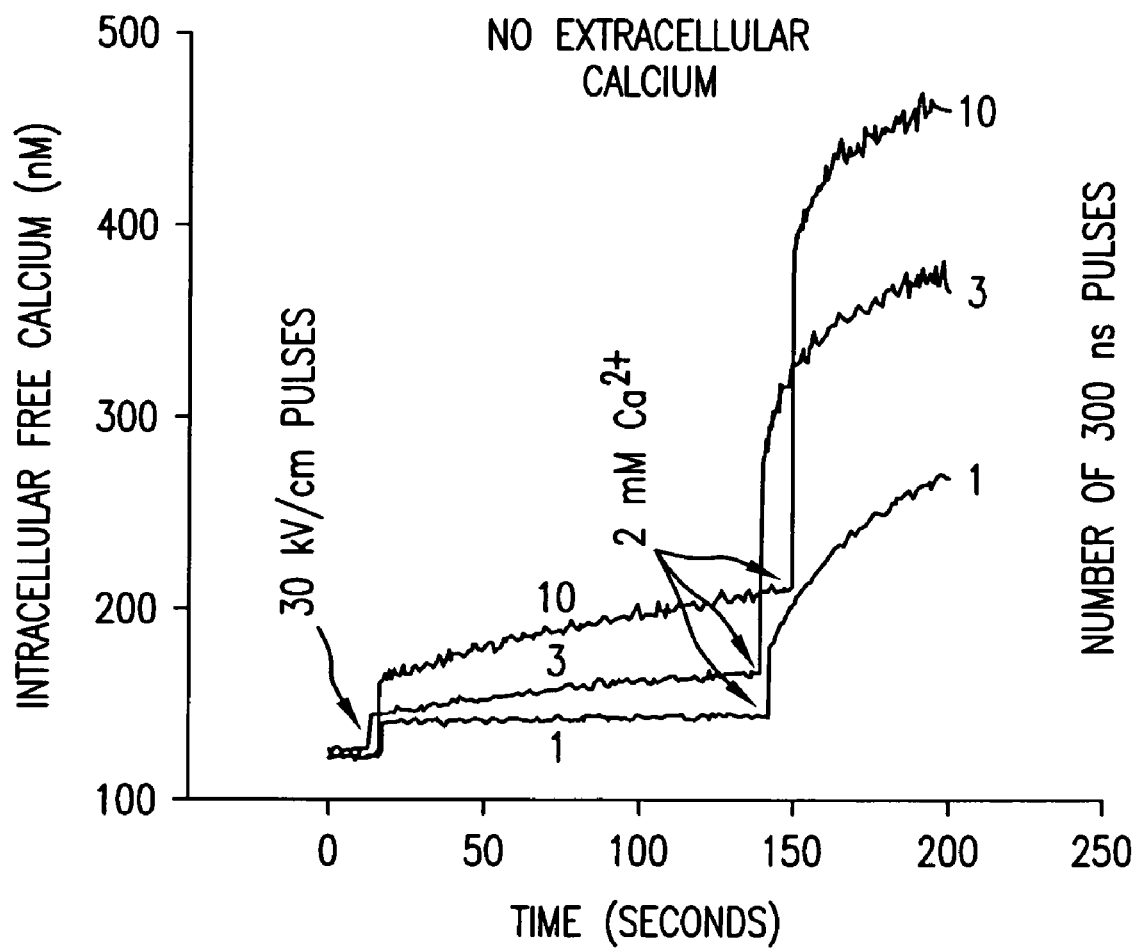
FIG. 19 shows that nsPEF pulses (300 ns and 30 kV/cm) cause calcium to be mobilized from intracellular stores in the absence of extracellular calcium, followed by capacitative calcium influx when calcium is added to the extracellular media. Fura-2 loaded cells were pulsed with 300 ns, 30 kV/cm pulses in the absence of extracellular calcium and the calcium concentration was determined in a fluorometer. After 2-3 minutes, 2 mM calcium was added to the extracellular media as the readings continued.
Figure 20:
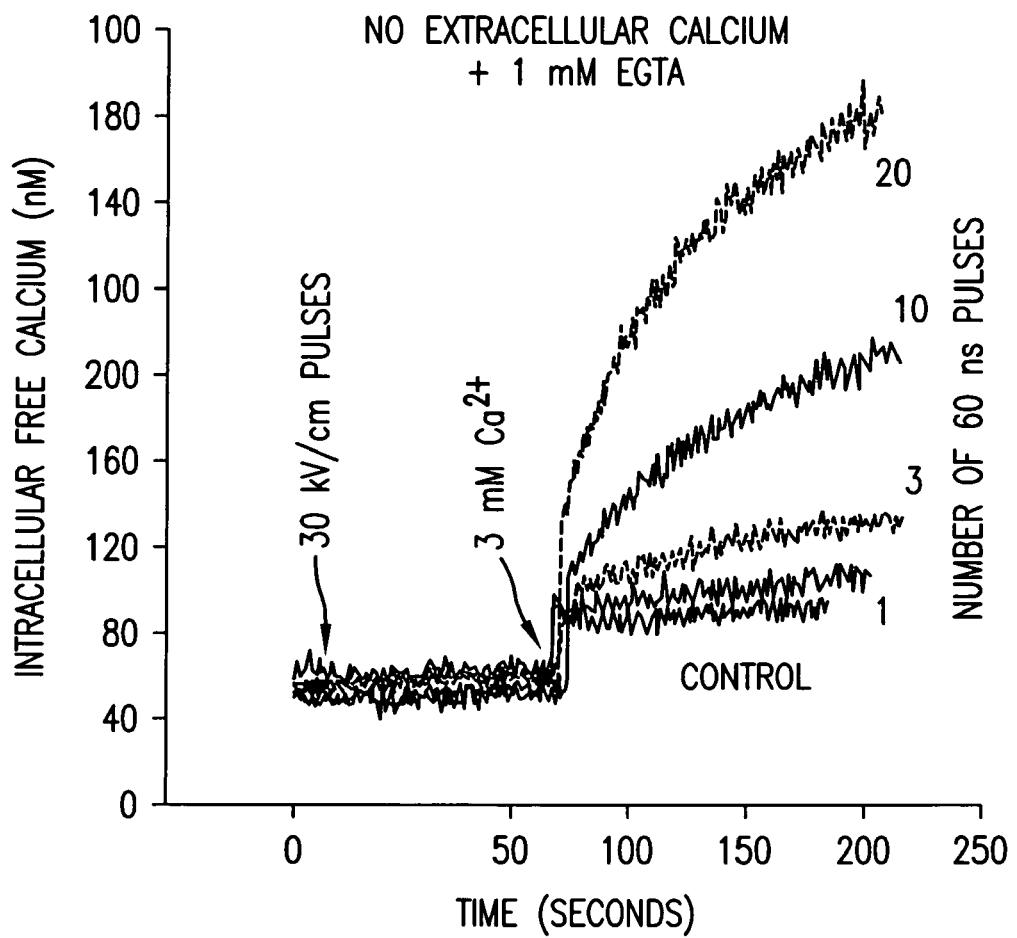
FIG. 20 shows that nsPEF pulses (60 ns and 30 kV/cm) cause calcium to be mobilized from intracellular stores in the absence of extracellular calcium, followed by capacitative calcium influx when calcium is added to the extracellular media. Fura-2 loaded cells were pulsed with 60 ns, 30 kV/cm pulses in the absence of extracellular calcium (and presence of 1 mM EGTA, a calcium chelator) and the calcium concentration was determined in a fluorometer. After 1-2 minutes, 3 mM calcium was added to the extracellular media as the readings continued.
Figure 21:
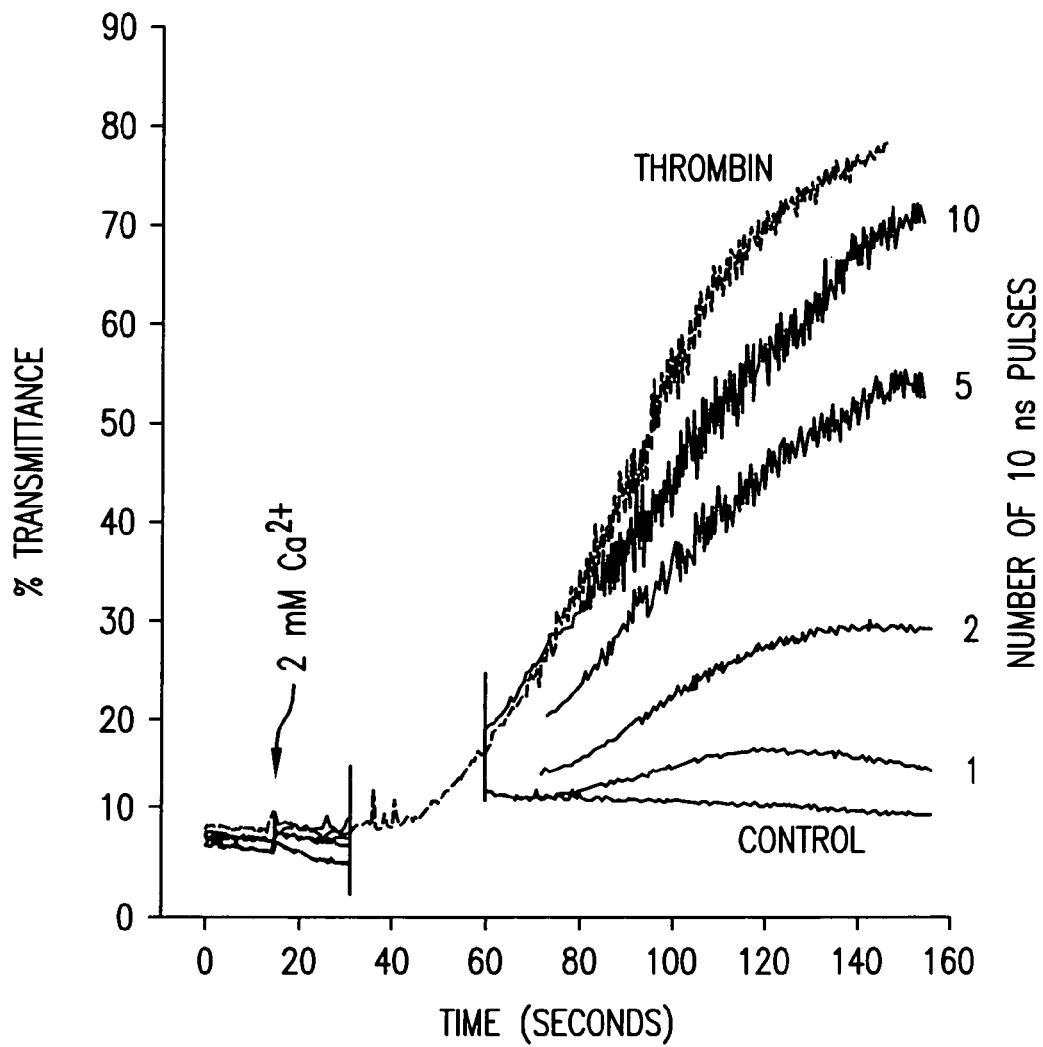
FIG. 21 shows that there is a pulse-dependent increase in platelet aggregation when platelets are pulsed at 125 kV/cm for 10 ns. Platelets were placed in the aggregometer, a baseline light transmittance measured, calcium was added at 15 seconds, then platelets were removed at 30 seconds into the pulsing cuvette. The platelets were pulsed 1, 2, 5 or 10 times for 10 ns each at 125 kV/cm. The platelets were then placed back into the aggregometer and aggregation measured. The 10 pulse treatment produced an aggregation response similar to that observed with 0.02 units/ml thrombin.
Figure 22:
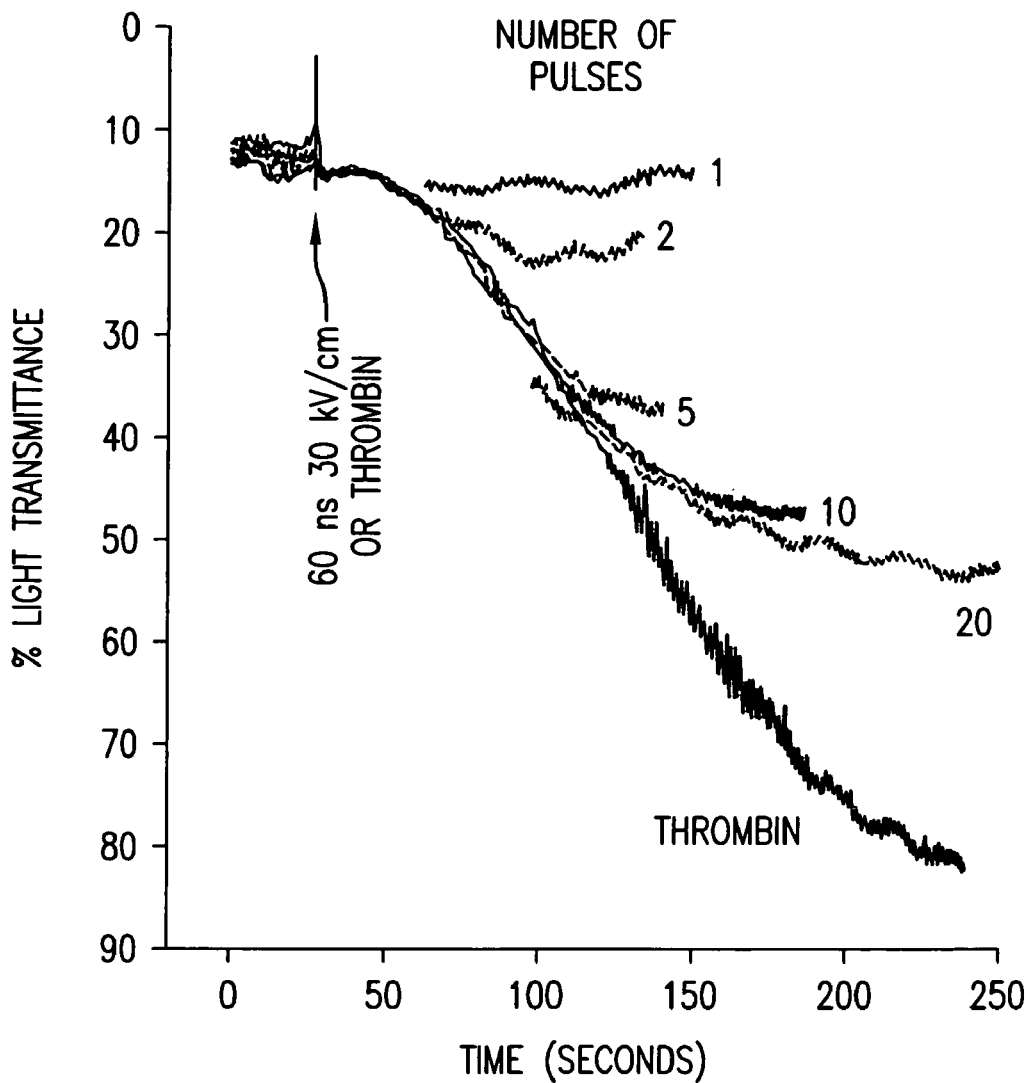
FIG. 22 shows that there is a pulse-dependent increase in platelet aggregation when platelets are pulsed at 30 kV/cm for 60 ns. Platelets were placed in the aggregometer, a baseline light transmittance measured, calcium was added at 25 seconds, then platelets were removed at 50 seconds, into the pulsing cuvette. The platelets were pulsed 1, 2, 5, 10, or 20 times for 60 ns each at 30 kV/cm. The platelets were then placed back into the aggregometer and aggregation measured. The 10 pulse treatment produced an aggregation response similar to that observed with 0.02 units/ml thrombin.

Calcium is mobilized from intracellular stores in the absence of extracellular calcium followed by capacitative calcium influx when calcium is added to the extracellular media, as shown in FIG. 19. Cells were loaded with the calcium indicator Fura-2, pulsed in the absence of extracellular calcium, and the calcium concentration was determined in a fluorometer. After 2-3 minutes, calcium was added to the extracellular media as the readings continued. The initial calcium mobilization was determined to come from intracellular stores of calcium. Studies with human HL-60 cells indicate that this calcium is released into the cytoplasm from the endoplasmic reticulum (ER) (White et al., 2004). When calcium was added to the extracellular media, a capacitative calcium influx through store-operated calcium channels in the plasma membrane (PM) was observed. This mimics the response to thrombin, which is known to release calcium from the ER, followed by capacitative calcium entry through store-operated channels in the PM. Similar results were observed with nsPEF-treated HL-60 cells in comparison with purinergic agonists (White et al., 2004) and in nsPEF-treated Jurkat cells in comparison with CD-3 stimulation. This is in contrast to results from studies with nsPEF-treated polymorphonuclear leukocytes (PMNs), where calcium entry is not through store-operated calcium channels in the PM. (Buescher et al., poster Bioelectromagnetics Society meeting June 2004).

nsPEF can cause platelets to aggregate in a manner similar to that observed with thrombin (FIG. 21). In particular, a pulse dependent increase in platelet aggregation was observed when platelets are pulsed at 125 kV/cm for 10 ns. Platelets were placed in the aggregometer, a baseline light transmittance measured, calcium was added at 15 seconds, then platelets were removed at 30 seconds into the pulsing cuvette. The platelets were pulsed 1, 2, 5 or 10 times for 10 ns each at 125 kV/cm. The platelets were then placed back into the aggregometer and aggregation measured. The 10 pulse treatment produced an aggregation response similar to that observed with 0.02 units/ml thrombin. When the duration of the nsPEF is increased, lower electric fields are needed to induce platelet activation and aggregation. Conversely, when the nsPEF duration is decreased, higher electric fields are required for this effect.

For these experiments, freshly isolated human platelets were incubated in a modified Tyrodes buffer containing calcium (as described in, e.g. Dobrydneva and Blackmore (2001)). The equipment used was a Chrono Log model 705 aggregometer. The data was recorded on a chart recorder and also digitized and saved on a computer hard drive. This was achieved by taking the optical signal and amplifying it 100 fold using a Tektronix® 5A22N differential amplifier. The amplified signal was then digitized using a DATAQ DI-194RS serial port data acquisition module and then sent to a P90 pentium computer running on Windows 95. The data were recorded using WinDaq/Lite waveform recording software (DATAQ instruments, Akron Ohio). The data were then analyzed using WinDaq waveform browser software.

Discussion

Recently, investigations of the effects of ultrashort, high intensity pulsed electric fields or nanosecond pulsed electric fields (nsPEF) on mammalian cells have demonstrated distinct differences on cell structure and function compared to classical plasma membrane electroporation. It was previously demonstrated that nsPEF invoked signal transduction mechanisms that initiate apoptosis cascades in several human cell lines including HL-60 cells (Beebe, S. J., et al. (2002) *IEEE Trans. Plasma Sci.* 30, 286-292; Beebe, S. J., et al. (2003) *FASEB J.* 17, 1493-1495). In the studies reported here, it was observed that at pulse durations and electric fields that are below the threshold for apoptosis and plasma membrane electroporation, nsPEF recruit signal transduction mechanisms that are similar to those utilized by natural ligands and chemical stimuli. Calcium mobilization induced by nsPEF, purinergic agonists, and thapsigargin exhibit similar kinetics and appear to utilize the same calcium channels present in intracellular and plasma membranes. Specifically, HL-60 cells exposed to nsPEF and UTP exhibited a rapid and transient increase in $[Ca^{2+}]_i$ in the absence of extracellular calcium and a rapid and more sustained increase in $[Ca^{2+}]_i$ in the presence of external calcium. Applications of nsPEF followed by UTP and UTP followed by nsPEF elicited less robust calcium mobilization compared to either stimulus alone, suggesting common sources for calcium mobilization. Based on UTP-stimulated calcium mobilization through PLC and IP$_3$, the nsPEF-stimulated intracellular calcium channel is expected to be in the endoplasmic reticulum and the plasma membrane channel is expected to be a capacitive calcium channel. These CCE channels are likely to be one or more of the TRP channels that are present in HL-60 cells (Heiner I., et al. (2003) *Biochem J.* 371, 1045-1053). These observations indicate that HL-60 cells do in fact sense and respond to nsPEF in a fashion that, at least in part, mimics the response seen with naturally occurring stimuli.

As described above, based on a simple electric model of the cell and from observations with human cells (Schoenbach, K. H., et al. (2001) *Bioelectromagnetics* 22, 440-448; Beebe, S. J., et al. (2002) *IEEE Trans. Plasma Sci.* 30, 286-292; Schoenbach, K. H., et al. (2002) *IEEE Transactions on Plasma Science* 30, 293-300; Beebe, S. J., et al. (2003) *FASEB J.* 17, 1493-1495; Deng, J., et al. (2003) *Biophys. J.* 84, 2709-2714; Vernier, P. T., et al. (2003) *Biochem. Biophys. Res. Commun.* 310, 286-295), as the pulse duration is decreased into the submicrosecond range (time domain), effects are less likely to occur on the plasma membrane and more likely to occur on subcellular membranes. Data reported here are consistent with the hypothesis that nsPEFs bypass the plasma membrane and exert effects primarily on internal cellular structures. The absence of PI uptake by cells exposed to nsPEF strongly suggests that calcium does not enter the cells through pores formed by classical plasma membrane electroporation. It could be argued that plasma membrane pores smaller than PI are present, but increases in intracellular calcium were observed in cells in the absence of calcium-containing media, indicating the release of calcium from intracellular structures. Additional support that nsPEFs affect intracellular structures and functions is provided by the observations that they induced an electric-field-dependent increase in capacitative calcium entry when calcium was added to cells in calcium-free media after exposure to the pulse. These findings provide additional evidence that nsPEFs alter intracellular structures without causing plasma membrane electroporation.

The increase in $[Ca^{2+}]_i$ in response to nsPEF demonstrates that this method of stimulation bypasses the plasma membrane and targets intracellular structures and functions. The mechanism(s) for HL-60 cell responses to nsPEF stimulation is still unknown, but the data presented suggests this perturbation does increase $[Ca^{2+}]_i$ reaching concentrations that are similar to a natural stimulus such as UTP. Furthermore, calcium elevations appear to reflect classical signaling kinetics. While not wanting to be limited to any one theory, several possible hypotheses may explain nsPEF effects on intracellular calcium levels.

One possibility is that nsPEF could form transient pores in endoplasmic reticulum and/or mitochondrial membranes. This would explain the increase in internal calcium levels since calcium would leak out of these organelles down its concentration gradient into the cytoplasm. This theory is supported by the theoretical calculations of Gowrishankar and Weaver (Gowrishankar, T. R., Weaver, J. C. (2003) *Proc. Natl. Acad. Sci. USA* 100: 3203-3208). The cell could interpret this intracellular calcium mobilization as a naturally occurring signal that then activates CCE in the plasma membrane. Propagation of this calcium signal could then be translated into increased gene expression through calcium-dependent transcription promoter mechanisms. The calcium signal could also increase protein translation events that are generally involved in regulation of signal transduction through post-translational modification of proteins. While ER electroporation remains a possibility, the relatively slow kinetics of calcium mobilization induced by nsPEF and UTP, as opposed to a much more rapid electroporation-induced calcium mobilization, suggests that intracellular membrane electroporation events may not be triggered by nsPEF.

A second possibility is that nsPEF pulse could be gating channels directly. Voltage-gated calcium channels could be likely candidates, but they have not been identified in HL-60 cells (Harper, J. L., et al. (2003) *Biochem. Pharmacol.* 65, 329-338). Furthermore, verapamil and diltiazem, which inhibit voltage-gated calcium channels, had no effect on nsPEF-induced increases in $[Ca^{2+}]_i$. Based on the potential source of the intracellular calcium, IP$_3$ receptors present in internal membranes are more possible candidates. IP$_3$ receptors and/or other calcium channels could be triggered by electric field-induced conformational changes that cause the channels to open. Even though the pulse duration is so short and the electric fields are relatively low (below the threshold for apoptosis), effects on conformational changes in proteins are possible.

Third, the nsPEF pulse could mimic a ligand signal that could trigger receptors on internal membranes thus causing calcium to be released from the internal stores into the cytoplasm. If the cell interpreted nsPEF as a ligand-binding event then releasing pooled internal calcium would generate the CCE events that were observed. Although effects on intracellular structures and functions are highly likely, additional effects may occur at the plasma membrane that are not measured. For example, nsPEF could trigger activation of the purinergic receptors or G-proteins in the plasma membrane. Alternatively, plasma membrane perturbations could activate PLC or otherwise trigger IP$_3$ release from membrane, causing calcium release from the endoplasmic reticulum. Additional studies are required to determine the mechanism(s) for nsPEF-induced calcium mobilization in HL-60 and other cells.

Since nsPEFs do not exist in nature, cells have evolved in the absence of these intense electric fields and/or these high frequencies. Nevertheless, the data reported here clearly indicate that cells have sensors that can respond to nsPEF. The data indicate that calcium mobilization does not occur by mechanisms that are related to classical plasma membrane electroporation, but more likely occurs by nsPEF-triggered effects on intracellular structures and functions as we have previously reported (Schoenbach, K. H., et al. (2001) *Bioelectromagnetics* 22, 440-448; Beebe, S. J., et al. (2002) *IEEE Trans. Plasma Sci.* 30, 286-292; Schoenbach, K. H., et al. (2002) *IEEE Transactions on Plasma Science* 30, 293-300; Beebe, S. J., et al. (2003) *FASEB J.* 17, 1493-1495). The nature of the cell sensor(s) remains to be determined, but it is clear that this sensor(s) is coupled to signal transduction mechanisms that mobilize intracellular calcium in ways that mimic natural ligands in HL-60 cells. nsPEF-induced calcium mobilization is not specific to HL-60 cells, but also has been observed in human Jurkat cells (Vernier, P. T., et al. (2003) *Biochem. Biophys. Res. Commun.* 310, 286-295). Whatever the mechanism, these studies show that nsPEFs can be used as stimuli to modulate signal transduction mechanisms that alter cell structure and function, and as shown here, to probe cellular mechanisms for calcium mobilization through intracellular calcium channels and CCE through the plasma membrane.

The foregoing detailed description includes many specific details. The inclusion of such detail is for the purpose of illustration only and should not be understood to limit the invention. In addition, features in one embodiment may be combined with features in other embodiments of the invention. Various changes may be made without departing from the scope of the invention as defined in the following claims. In addition, all non-priority patents and other references cited herein are indicative of the level of skill in the art and are hereby incorporated by reference in their entirety.

What is claimed is:

1. A method for inducing calcium mobilization in cells comprising applying at least one nanosecond pulsed electric field (nsPEF) to the cells, whereby calcium is mobilized in said cells, wherein said at least one nsPEF has a pulse duration of at least about 100 picoseconds and no more than about 1 microsecond and an electric field strength of at least about 10 kV/cm and no more than about 350 kV/cm, wherein said cells are platelets.

2. The method of claim 1, whereby calcium influx into said cells occurs.

3. The method of claim 1, wherein said at least one nsPEF has a pulse duration of at least about 100 picoseconds and no more than about 1 microsecond and an electric field strength of at least about 10 kV/cm and no more than about 30 kV/cm.

4. The method of claim 1, wherein said at least one nsPEF has a pulse duration of at least about 100 picoseconds and no more than about 1 microsecond and an electric field strength of at least about 10 kV/cm and no more than about 125 kV/cm.

5. The method of claim 1, wherein said at least one nsPEF has a pulse duration of at least about 10 nanoseconds and no more than about 300 nanoseconds and an electric field strength of at least about 10 kV/cm and no more than about 30 kV/cm.

6. The method of claim 1, wherein said at least one nsPEF has a pulse duration of at least about 10 nanoseconds and no more than about 300 nanoseconds and an electric field strength of at least about 10 kV/cm and no more than about 125 kV/cm.

7. The method of claim 1, wherein said at least one nsPEF has a pulse duration of about 10 nanoseconds and an electric field strength of about 125 kV/cm.

8. The method of claim 1, wherein said at least one nsPEF has a pulse duration of about 60 nanoseconds and an electric field strength of about 30 kV/cm.

9. The method of claim 1, wherein at least two nsPEFs are applied.

10. The method of claim 1, wherein at least five nsPEFs are applied.

11. The method of claim 1, wherein at least ten nsPEFs are applied.

12. The method of claim 1, wherein said cells are suspended in a medium.

13. The method of claim 1, wherein said cells are included in a tissue.

14. The method of claim 2, wherein said cells are human platelets and whereby activation and aggregation of said platelets is induced.

15. A method for increasing intracellular calcium in cells comprising applying at least one nanosecond pulsed electric field (nsPEF) to the cells, whereby intracellular calcium in said cells is increased, wherein said at least one nsPEF has a pulse duration of at least about 100 picoseconds and no more than about 1 microsecond and an electric field strength of at least about 10 kV/cm and no more than about 350 kV/cm, wherein said cells are platelets.

16. The method of claim 15, wherein said cells are human platelets and whereby activation and aggregation of said platelets is induced.

17. A method for activating and aggregating human platelets comprising applying at least one nanosecond pulsed electric field (nsPEF) to the platelets, whereby said platelets are activated and induced to form aggregates, wherein said at least one nsPEF has a pulse duration of at least about 100 picoseconds and no more than about 1 microsecond and an electric field strength of at least about 10 kV/cm and no more than about 350 kV/cm.

18. The method of claim 17, wherein said at least one nsPEF has a pulse duration of about 10 nanoseconds and an electric field strength of about 125 kV/cm.

19. The method of claim 17, wherein said at least one nsPEF has a pulse duration of about 60 nanoseconds and an electric field strength of about 30 kV/cm.

20. The method of claim 17, wherein said platelets are suspended in a medium.

21. The method of claim 17, wherein said platelets are included in a tissue.

22. A method for treating an injury, trauma, or the loss of blood in a subject, comprising applying at least one nsPEF to platelets at the site of injury, trauma, or blood loss, whereby said platelets are activated and induced to form aggregates, wherein said at least one nsPEF has a pulse duration of at least about 100 picoseconds and no more than about 1 microsecond and an electric field strength of at least about 10 kV/cm and no more than about 350 kV/cm.

23. A method of treating an injury, trauma, or the loss of blood in a subject, comprising applying at least one nsPEF to autologous platelets, whereby said platelets are activated and induced to form aggregates, wherein said activated and aggregated platelets are applied to the site of injury, trauma, or blood loss, wherein said at least one nsPEF has a pulse duration of at least about 100 picoseconds and no more than about 1 microsecond and an electric field strength of at least about 10 kV/cm and no more than about 350 kV/cm.

24. The method of claim 22 or claim 23, wherein said blood loss is related to a bleeding disorder resulting from inactive platelets or low platelet counts.

25. The method of claim 22 or claim 23, wherein said blood loss is related to a platelet disorder selected from the group consisting of congenital afibrinogenemia, Glanzmann's thrombasthenia, gray platelet syndrome, and Hermansky-Pudlak syndrome.

* * * * *